United States Patent
Menhardt et al.

(10) Patent No.: US 11,977,088 B2
(45) Date of Patent: May 7, 2024

(54) HISTORY LOGGING FOR SAMPLES OF BIOLOGICAL MATERIAL

(71) Applicant: Beckman Coulter, Inc., Brea, CA (US)

(72) Inventors: Wido Menhardt, Los Gatos, CA (US); Matthew Hanson, Orange, CA (US); Anthony Camisa, Anaheim Hills, CA (US)

(73) Assignee: Beckman Coulter, Inc., Brea, CA (US)

( * ) Notice: Subject to any disclaimer, the term of this patent is extended or adjusted under 35 U.S.C. 154(b) by 1263 days.

(21) Appl. No.: 16/313,704

(22) PCT Filed: Jun. 16, 2017

(86) PCT No.: PCT/US2017/037860
§ 371 (c)(1),
(2) Date: Dec. 27, 2018

(87) PCT Pub. No.: WO2018/005129
PCT Pub. Date: Jan. 4, 2018

(65) Prior Publication Data
US 2019/0331702 A1    Oct. 31, 2019

Related U.S. Application Data

(60) Provisional application No. 62/355,165, filed on Jun. 27, 2016.

(51) Int. Cl.
*G01N 35/00* (2006.01)
*B01L 9/06* (2006.01)
*G16H 10/40* (2018.01)

(52) U.S. Cl.
CPC ......... *G01N 35/00613* (2013.01); *B01L 9/06* (2013.01); *G01N 35/00712* (2013.01);
(Continued)

(58) Field of Classification Search
CPC ....... G01N 35/00613; G01N 35/00712; G01N 35/00871; G01N 2035/00752;
(Continued)

(56) References Cited

U.S. PATENT DOCUMENTS 10,342,737 B1 * 7/2019 Shanmugavelayudam ............... A61J 1/165
2006/0208881 A1    9/2006 Suzuki
(Continued)

FOREIGN PATENT DOCUMENTS

CN    102298714 A    12/2011
EP    2668847 A1    12/2013
(Continued)

OTHER PUBLICATIONS

International Search Report and Written Opinion dated Sep. 22, 2017 for International Application No. PCT/US2017/037860, 10 pages.
(Continued)

*Primary Examiner* — Jill A Warden
*Assistant Examiner* — John McGuirk
(74) *Attorney, Agent, or Firm* — Frost Brown Todd LLP

(57) ABSTRACT

A method of reducing quality problems associated with patient sample collection and delivery is provided. It is possible that the method can provide a chain of custody process to better track a sample from the initial point of sample collection to the final point of sample testing. Such a method can also include providing an alert to indicate a potential problem with the quality of the diagnostic test result when a measured parameter exceeds a threshold.

18 Claims, 8 Drawing Sheets

(52) U.S. Cl.
CPC ....... *G01N 35/00871* (2013.01); *G16H 10/40* (2018.01); *B01L 2200/14* (2013.01); *B01L 2200/146* (2013.01); *B01L 2200/147* (2013.01); *B01L 2200/185* (2013.01); *B01L 2300/021* (2013.01); *B01L 2300/023* (2013.01); *B01L 2300/024* (2013.01); *B01L 2300/0663* (2013.01); *G01N 2035/00752* (2013.01); *G01N 2035/00851* (2013.01)

(58) Field of Classification Search
CPC ... G01N 2035/00851; G01N 2001/007; G01N 35/00584; B01L 9/06; B01L 2200/14; B01L 2200/146; B01L 2200/147; B01L 2200/185; B01L 2300/021; B01L 2300/023; B01L 2300/024; B01L 2300/0663; B01L 2200/143; B01L 2200/18; G16H 10/40; G16H 40/20; G16H 40/67; G06Q 10/0832; G06Q 10/0833; B65D 79/02
See application file for complete search history.

(56) References Cited

U.S. PATENT DOCUMENTS

| | | | |
|---|---|---|---|
| 2009/0075367 | A1 | 3/2009 | Bennett |
| 2010/0253519 | A1* | 10/2010 | Brackmann .............. B60P 3/03 340/572.1 |
| 2013/0123089 | A1 | 5/2013 | Johns et al. |
| 2014/0171829 | A1 | 6/2014 | Holmes et al. |
| 2016/0363605 | A1* | 12/2016 | Liepold ................... F24F 3/167 |
| 2018/0128718 | A1* | 5/2018 | Crum ..................... B01L 3/545 |

FOREIGN PATENT DOCUMENTS

| | | | |
|---|---|---|---|
| JP | 2004-341829 A | 12/2004 | |
| JP | 2006-004299 A | 1/2006 | |
| JP | 2013-130398 A | 7/2013 | |
| WO | WO-2006124105 A2 * | 11/2006 | ............... B60P 3/03 |
| WO | WO 2017/149468 A1 | 9/2017 | |

OTHER PUBLICATIONS

International Preliminary Report on Patentability dated Jan. 1, 2019 for International Application No. PCT/US2017/037860, 7 pages.

Japanese Office Action, Notice of Reasons for Refusal, and Search Report dated Oct. 13, 2020 for Application No. JP 2019-519967, 35 pgs.

Chinese Office Action for CN Patent Application No. 201780039961. 5, dated Nov. 24, 2022, 10 pages.

* cited by examiner

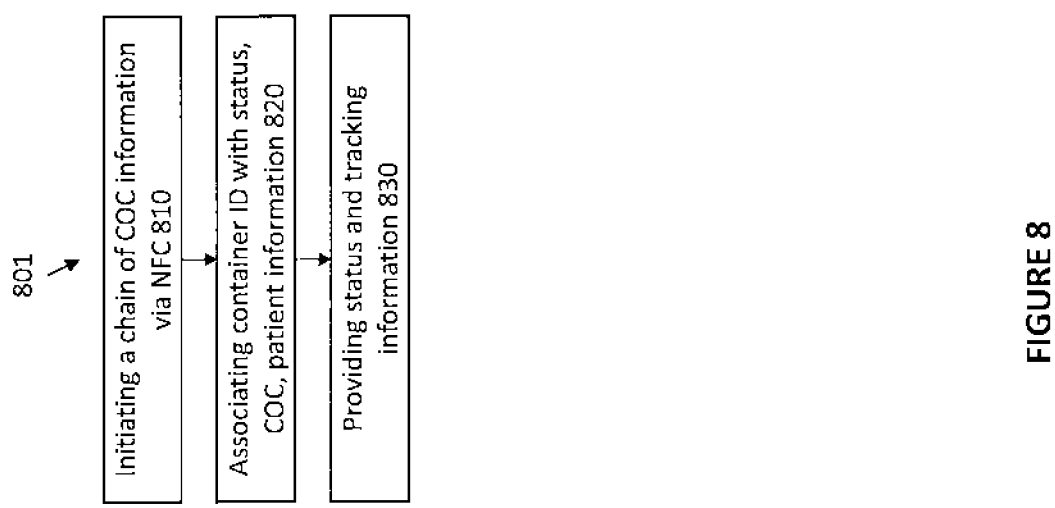

HISTORY LOGGING FOR SAMPLES OF BIOLOGICAL MATERIAL

This application is a National Stage Entry of PCT Application No. PCT/US17/37860, entitled "History Logging for Samples of Biological Material," filed Jun. 16, 2017, which claims priority to U.S. Provisional Application No. 62/355,165, entitled "History Logging for Samples of Biological Material," filed Jun. 27, 2016, the disclosures of which are incorporated by reference herein.

TECHNICAL FIELD

The invention relates to sample management. In one aspect, the invention relates to techniques for managing biological samples from point of collection to point of testing, and through disposal.

BACKGROUND

Laboratories routinely collect biological samples from patients, and transport the samples to examination sites for analysis. From the point-of-collection (POC) site to the point-of-testing (POT) site, each sample is exposed to different conditions. The sample may be subjected to handling by various individuals and equipment and exposed to different conditions from the moment of collection, through transport, reception, analysis and disposal. At the POC site, a patient sample is collected, identified and entered into a database. The sample is then transported via a courier, who often makes multiple stops of picking up and delivering additional samples. The sample is then delivered to a POT site or medical testing laboratory for analysis.

Despite advances in technology and increased point-of-care testing, the vast majority of samples are collected in one place and transported to another for analysis, with handling at any point. Some tests are available only in certain reference POT sites, thereby requiring samples to be transported over long distances. In some instances, transport involves multiple stops, before the sample arrives at the POT. These additional stops further prolong the samples being potentially exposed to uncontrolled environments. Some biological samples have to be kept at a controlled condition to preserve the quality of the samples. For instance, blood samples have to be kept cool to preserve their stability and quality. Sample transport and storage conditions, together with the transport time interval between POC and POT sites, can have an impact on the results of tests performed on the samples. Erroneous test results not only require sample recollection, transport and analysis, they could also cause a healthcare provider to provide wrong diagnosis or treatments. Accordingly, an improved sample management system is needed.

SUMMARY

In general, the technology disclosed herein can be used to implement systems and methods maintaining history logs for samples from POC through POT. For example, in a first aspect, the disclosed technology can be used to implement a machine which comprises a sample transport container, one or more environment sensors, a sample manager located at a testing location, and a set of history loggers. In such a machine, the sample transport container can be adapted to store and enable transport of a plurality of sample holders for samples of biological materials collected from patients. The set of environment sensors can be adapted to take measurements one or more characteristics of an environment of the sample transport container. The sample manager located at the testing location may be programmed to, for each sample of biological material transported in the sample transport container, make history logging information for that sample of biological material available at the testing location. Such history logging information may be taken from a set of history logs, each of which is associated with a single sample of biological material with a unique identifier. Such history logs may comprise a set of measurements of the characteristics of the environment of the sample transport container while the associated sample of biological material was in transit, and/or a transit initiation timestamp, wherein the transit initiation timestamp is when the associated sample of biological material was placed into the sample transport container for transit. Additionally, in this type of machine, the history loggers from the set of history loggers may be programmed to receive, for inclusion in the history logs of samples of biological material handled by users of the history loggers, transit data for those samples of biological material.

In a second aspect, a machine such as described in the context of the first aspect could be implemented such that the set of one or more environment sensors adapted to take measurements of one or more characteristics of the environment of the sample transport container comprise one or more pressure sensors adapted to take atmospheric pressure measurements of the environment of the sample transport container, and one or more temperature sensors adapted to take temperature measurements of the environment of the sample transport container. In this aspect, it is also possible that the history logging information the sample manager located at the testing location is programmed to make available at the testing location for a sample of biological material comprises how many individuals have handled the sample of biological material while in transit, duration of time the sample of biological material is in transit, atmospheric pressure the sample of biological material has been exposed to while in transit, and temperature the sample of biological material has been exposed to while in transit.

In a third aspect, a machine such as described in the context of the first or second aspects could be implemented such that the sample manager located at the testing location is programmed to, when a determination of whether a sample of biological material does not conform to a set of requirements for a medical diagnostic test indicates that the sample of biological material does not conform to the set of requirements for the medical diagnostic test, provide an alert. Such an alert could be selected from a group consisting of an instruction to evaluate a result of the medical diagnostic test using a modified evaluation parameter, an instruction to rerun the medical diagnostic test with the sample of biological material one or more times, an instruction to discard the sample of biological material, and an instruction to generate an order to collect another sample to perform the medical diagnostic test.

In a fourth aspect, a machine such as described in the context of the third aspect could be implemented such that the set of one or more environment sensors adapted to take measurements of one or more characteristics of the environment of the sample transport container could comprise one or more pressure sensors adapted to take atmospheric pressure measurements of the environment of the sample transport container, and one or more temperature sensors adapted to take temperature measurements of the environment of the sample transport container. Similarly, a machine implemented according to the fourth aspect could comprise a central monitor programmed to maintain the set of history logs by performing acts comprising receiving transit data from history loggers for samples of biological material and storing the transit data for samples of biological material in database records associated with the unique identifiers of the samples of biological material to which the transit data relates. Additionally, such a central monitor could be programmed to make the determination of whether the sample of biological material does not conform to the set of requirements for the medical diagnostic test by performing a set of acts. Such a set of acts could comprise, using the unique identifier of the sample of biological material, retrieving data indicating that the medical diagnostic test is to be performed with that sample of biological material. Such a set of acts could also comprise comparing temperature data from the set of one or more temperature sensors with a temperature threshold associated with the medical diagnostic test. Such a set of acts could also comprise comparing atmospheric pressure data from the set of one or more pressure sensors with an atmospheric pressure threshold associated with the medical diagnostic test. Such a set of acts could also comprise comparing how long the sample of biological material had been in transit with a transit time threshold associated with the medical diagnostic test. Such a set of acts could also comprise comparing a time delay between when the sample of biological material was collected and when it was placed in transit with a collection delay threshold for the medical diagnostic test.

In a fifth aspect, a machine such as described in the context of any of the first through fourth aspects could include a central monitor programmed to maintain the set of history logs by performing acts comprising incorporating data received from the history loggers into database records associated with unique identifiers of samples of biological material to which that data relates. In this fifth aspect, the set of one or more history loggers could comprise a first sample manager located at a collection point for samples of biological material and a second sample manager located at a preparation site for samples of biological material. The first sample manager could be programmed to send to the central monitor, for each sample of biological material collected at the collection point where the first sample manager is located, a timestamp reflecting when that sample of biological material was collected and a unique identifier for that sample of biological material. The second sample manager could be programmed to, for each sample of biological material received at the preparation site where the second sample manager is located: (i) retrieve, from the central manager using the unique identifier for that sample of biological material, a set of preparation activities to perform for that sample of biological material, and (ii) present instructions to perform the set of preparation activities for that sample of biological material.

In a sixth aspect, a machine such as described in the context of the fifth aspect could be implemented such that each history logger from the set of one or more history loggers is programmed to require a user of that history logger to authenticate his or her identity before the history logger could receive information about samples of biological material taken from patients or communicate information about samples of biological material taken from patients with either the central monitor or other history loggers. Each of the history loggers could also be programmed to inform the central monitor of the authenticated identity of the user of that history logger and the unique identifiers of samples of biological material handled by the user of that history logger. Similarly, in this sixth aspect, a central monitor could also be programmed to, based on receiving a message that a sample of biological material has arrived at the testing location using the sample identifier for the sample of biological material, retrieve data indicating the authenticated identifiers of all users of history loggers who had handled the sample of biological material.

In a seventh aspect, a machine such as described in the context of any of the first through sixth aspects could be implemented such that the unique identifiers for the samples of biological material in the history logs comprise, for each sample of biological material transported in the sample transport container, either an identifier of a sample holder in which that sample of biological material is contained, an identifier of the sample transport container combined with an identification of a location in the sample transport container where the sample of biological material is placed, or both.

In an eighth aspect, a machine such as described in the context of any of the first seven aspects could be implemented such that the sample manager located at the testing location is one of a plurality of sample managers located at a plurality of testing locations, the set of one or more history loggers comprises a plurality of mobile history loggers, and the machine comprises a central monitor communicatively connected to each of the testing locations. In this aspect, the central monitor could be configured to determine a testing location to which a sample of biological material should be transported and send a message indicating the testing location to which the sample of biological material should be transported to a mobile history logger of a courier for the sample of biological material. In this type of implementation, the determination of a testing location to which a sample of biological material should be transported could be based on testing time at each of the plurality of testing locations, distance between the sample of biological material and each of the plurality of testing locations, and/or transit time to each of the plurality of testing locations.

In a ninth aspect, a machine such as described in the context of any of the first through eighth aspects could be implemented such that the set of one or more history loggers comprises a plurality of mobile history loggers, each of which comprises either a wireless transceiver or a wireless receiver and wireless transmitter. In a machine implemented according to this ninth aspect, the sample manager at the testing location could be programmed to receive the set of history logs from a mobile history logger carried by a courier who delivers the sample transport container to the testing location. Additionally, in a machine implemented according to this ninth aspect, the set of one or more history loggers could be adapted to maintain the set of history logs using instructions which, when executed by a history logger, cause the history logger which executes the instructions to perform acts comprising: (i) when a user of that history logger takes possession of a sample of biological material from a previous custodian of the sample of biological material, receiving, via a first NFC connection, the history log for the sample of biological material from a history logger used by the previous custodian of the sample of biological material; (ii) updating the history log for the sample of biological material with a timestamp indicating when the user of that history logger takes possession of the sample of biological material; and (iii) when the user of that history logger transfers possession of the sample of biological material to a new custodian, transferring, via a second NFC connection, the history log for the sample of biological material to a history logger used by the new custodian.

The disclosed technology could also be used in the performance of methods. For example, in a tenth aspect, the disclosed technology can be used to perform a method which comprises storing a set of programs on one or more non-transitory computer readable mediums, and making a plurality of programs taken from that set available for reproduction and use. In such a method, the plurality of programs made available for reproduction and use could comprise first and second programs respectively operable to, when executed, cause a history logger to perform a set of history logging acts, and cause a sample manager to perform a set of sample management acts. The history logging acts could comprise receiving transit data comprising values of environment characteristics for a sample transit container while samples of biological materials are in transit in the sample transport container. The sample management acts could comprise receiving a unique identifier corresponding to a sample of biological material, and making history logging information for the sample of biological material corresponding to the received unique identifier available at a location where the sample of biological material is to be tested and/or prepared for testing. In this aspect, the set of history logging information could include a value of at least one of the environment characteristics the first program is operable to cause the history logger to receive when executed, and a period since initiation of transit for the sample of biological material corresponding to the received unique identifier.

In an eleventh aspect, a method such as described in the context of the tenth aspect could be implemented in which the set of programs comprises a third program, and where the third program is operable to, when executed, cause a central monitor to perform a set of central monitor acts. Such central monitor acts could comprise maintaining a set of history logs associated with samples of biological material and responding to requests received from sample managers for information on samples of biological material corresponding to unique identifiers associated with the data records in which the received transit data was stored. In this aspect, maintaining the set of history logs could be done by performing acts comprising receiving transit data for the samples of biological material from the history logger and using the received transit data to update a database comprising records associated with unique identifiers corresponding to samples of biological material to which the received transit data relates.

In a twelfth aspect, a method such as described above in the context of the eleventh aspect could be performed in which the history logger is a smartphone configured with the first program, the sample manager is a computer configured with the second program, the central monitor is a server configured with the third program, and the central monitor is configured to determine a distance between the history logger and the sample manager using a GPS receiver incorporated into the history logger.

In a thirteenth aspect, a method such as described in the context of the eleventh or twelfth aspects could be performed in which the method comprises at least one of the acts of making the third program available for reproduction and use and/or executing the third program.

In a fourteenth aspect, a method such as described in the context of any of the eleventh through thirteenth aspects could be performed in which at least one of the programs from the set of programs is operable to, when executed, cause a computer to perform acts comprising determining whether the sample of biological material conforms to a set of requirements for a medical diagnostic text and, when the determination of whether the sample of biological material conforms to a set of requirements for the medical diagnostic test indicates that the sample of biological material does not conform to the set of requirements for the medical diagnostic test, provide an alert. In such a method, the determination of whether the sample of biological material conforms to the set of requirements for a medical diagnostic test could be performed by: (i) using the unique identifier for the sample of biological material, retrieving data indicating that the medical diagnostic test is to be performed with that sample of biological material; (ii) comparing temperature data from the database which execution of the third program would cause the central monitor to update with a temperature threshold associated with the medical diagnostic test; (iii) comparing atmospheric pressure data from the database which execution of the third program would cause the central monitor to update with an atmospheric pressure threshold associated with the medical diagnostic test; (iv) comparing how long the sample of biological material had been in transit with a transit time threshold associated with the medical diagnostic test; and (v) comparing a time delay between when the sample of biological material was collected and when it was placed in transit with a collection delay threshold for the medical diagnostic test. Additionally, in a method of the fourteenth aspect, the alert may be selected from a group consisting of an instruction to evaluate a result of the medical diagnostic test using a modified evaluation parameter, an instruction to rerun the medical diagnostic test with the sample of biological material one or more times, an instruction to discard the sample of biological material, and an instruction to generate an order to collect another sample to perform the medical diagnostic test.

In a fifteenth aspect, a method such as described in the context of the fourteenth aspect could be performed in which at least one of the programs form the plurality of programs made available for reproduction and use which is operable to, when executed, cause the computer to perform a set of alerting acts is selected from a group of programs consisting of the second program and the third program.

In a sixteenth aspect, a method such as described in the context of any of the tenth through fifteenth aspects could be performed wherein the history logger is a mobile history logger and the first program is operable to perform acts to facilitate transfer of a transported sample of biological material from a first custodian using the history logger to a second custodian using a second history logger configured by the first program. In this type of method, the mobile history logger could be configured to authenticate an identity of its user with biometric information from that user and could comprise either a wireless transceiver, a wireless receiver paired with a wireless transmitter, or both. Similarly, in this type of method, the acts which the first program could be operable to perform to facilitate transfer could comprise (i) causing the history logger to send, via a NFC connection, a history log for the transported sample of biological material to a second history logger, and (ii) causing the second history logger to update the history log for the transported sample of biological material with a timestamp indicating when the second custodian takes possession of the sample of biological material.

In a seventeenth aspect, the disclosed technology could be used to implement a set of computer programs stored on one or more devices which, when executed, cause performance of the method steps described in the context of any of the tenth through sixteenth aspects.

Further information on how the disclosed technology could potentially be implemented is set forth herein, and variations on the sample will be immediately apparent to and could be practiced without undue experimentation by those of ordinary skill in the art based on the material which is set forth in this document. Accordingly, the exemplary methods and machines described in this summary should be understood as being illustrative only, and should not be treated as limiting on the scope of protection provided by this or any related document.

BRIEF DESCRIPTION OF DRAWINGS

FIG. 8 is a flow chart illustrating the use of NFC communication to manage a sample chain of custody in accordance with one embodiment of the present disclosure.

DETAILED DESCRIPTION

The technology disclosed herein can be used to address problems related to the transport of biological materials from a point of collection through their testing, as well as problems related to the testing of those materials at a test location (e.g., properly interpreting test results in light of the environment a sample may have been exposed to during transport), and even to their disposal after testing is complete. For the purpose of illustration, this document focuses on the application of the inventors' technology in that context. However, it should be understood that the technology disclosed herein could be used for other purposes and in other contexts as well. For example, rather than being used in the context of transporting biological materials, the disclosed technology could be applied in the context of transporting chemicals of non-biological origin. Similarly, rather than simply being used for testing of materials, the disclosed technology could be applied when materials are used for other purposes, such as where biological materials are used in a manufacturing or other industrial setting. Accordingly, the present description should be understood as being provided only by way of illustrative example, and numerous modifications and alternate embodiments of the invention will occur to those skilled in the art.

Figure 1:
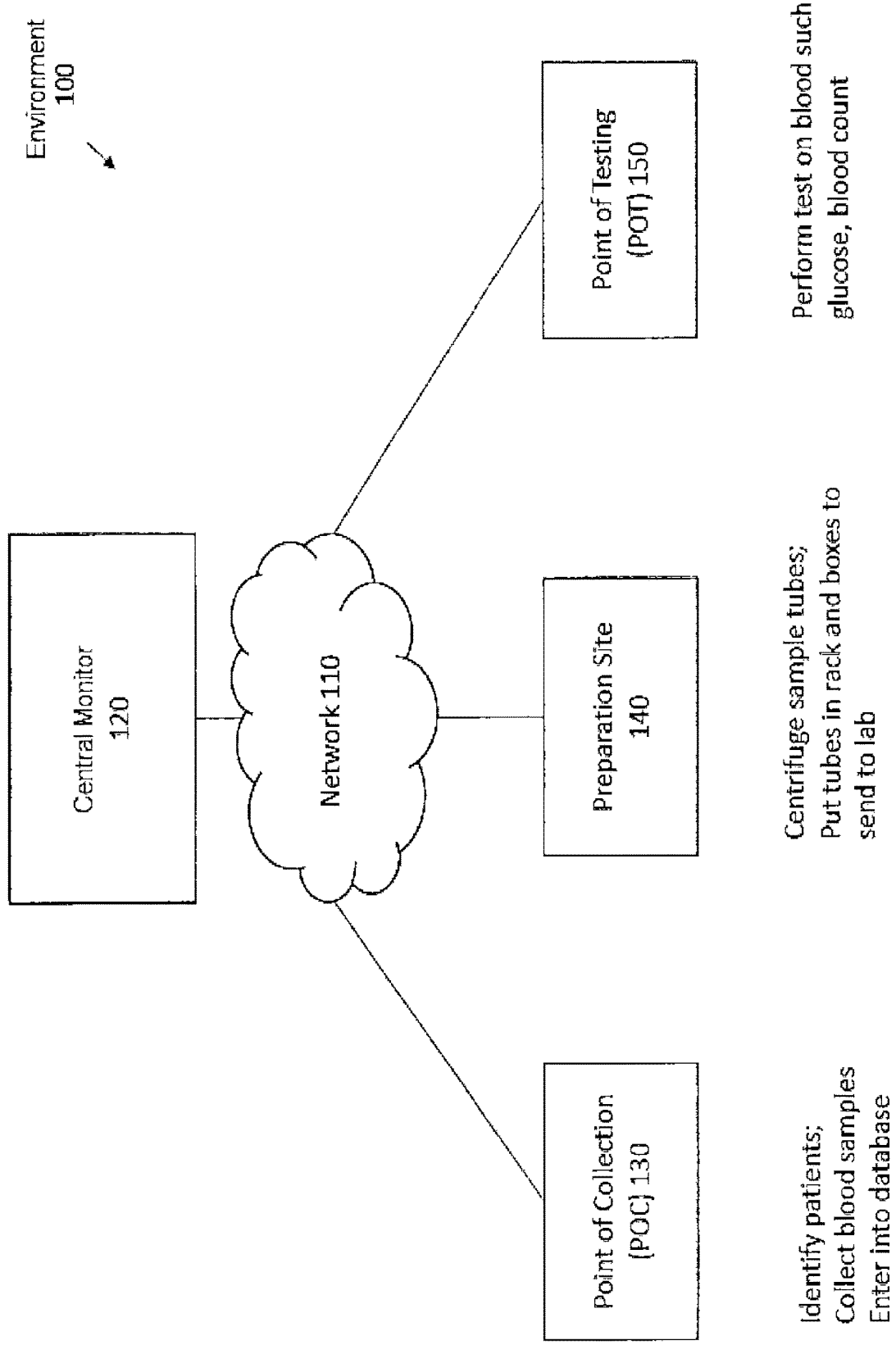
FIG. 1 is a diagram illustrating an environment in which aspects of the disclosed technology could be practiced.

Turning now to the figures, FIG. 1 is a block diagram illustrating an exemplary environment 100 in which aspects of the disclosed technology can be deployed to assist various healthcare and laboratory facilities with exchanging information and keeping track of biological samples. Environment 100 includes a network 110, a central monitor 120, a collection point/point of collection (POC) 130, a preparation site 140, and a testing location/point of testing (POT) site 150. It should be noted that the network 110 depicted in FIG. 1 may be only one of a plurality of networks connecting the various sites and systems in which the disclosed technology would be practiced. For example, the POC 130, preparation site 140 and POT 150 may be connected to each other by a local area network (LAN), or a wide area network (WAN), while the network 110 connecting those sites to the central monitor 120 could be a separate dedicated network intended for secure communication of information between remote locations, or could be a segmented aspect of some greater network (e.g., an encrypted virtual private network running over a public WAN). In an embodiment where one or more of the depicted sites are connected by a LAN, that LAN may be a network within a single facility such as a hospital comprising various departments such as an emergency room, a pharmacy department, and a laboratory, etc. Similarly, in an embodiment where one or more of the depicted sites are connected by a WAN, the WAN may be a worldwide network comprising different entities that are separate and independent of one another (e.g., the Internet). Of course, it should be understood that having a POC 130, preparation site 140 and POT 150 connected via a network which is either physically or logically separate from the network 110 is not a requirement for use of the disclosed technology, and that it is possible that network 110 could be used for all communications between entities in an environment 100 such as shown in FIG. 1.

Figure 4:
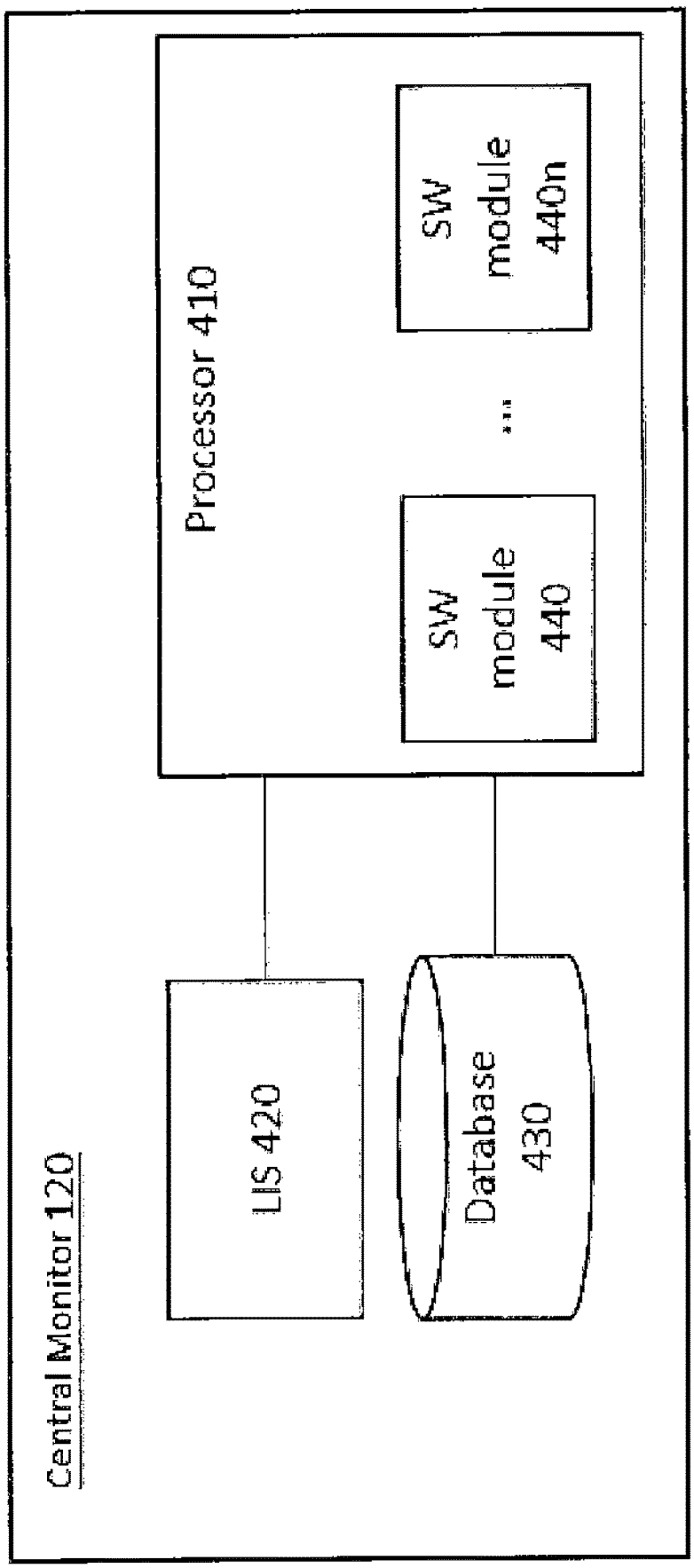
FIG. 4 is a diagram providing information about a central monitor which could be included in some embodiments of the disclosed technology.

Turning now to the individual items illustrated in the environment 100 of FIG. 1, FIG. 4 illustrates a detailed block diagram of central monitor 120 according to one aspect of the present disclosure. In one embodiment, central monitor 120 can be implemented using a computer which includes processor 410 that would execute instructions that could be organized into one or more software modules 440-440n, and that could configure the central monitor 120 to perform actions such as receiving information about biological samples, tracking that information using unique identifier(s) for those samples, maintaining history logs which tie that information to samples using their unique identifier(s), and distributing that information or instructions based on that information as needed in the relevant environment 100. Software modules 440-440n which could be used to configure a central monitor 120 such as shown in FIG. 4 could also allow the central monitor 120 to perform various laboratory functions, such as scheduling test runs, validating and verifying test results, and performing a custom set of rules. Additionally, as shown in FIG. 4, a central monitor 120 can include a database 430 and a laboratory information system (LIS) 420. Database 430 may include patient records, patient information, laboratory tests, and trends, and may be a relational database, object-oriented database or other suitable data storage structure.

It should be understood that, while FIG. 4 illustrates a central monitor 120 as a single integrated system, embodiments of the disclosed technology which include a central monitor 120 may not implement that item in precisely the manner illustrated in FIG. 4. For example, in various embodiments, a central monitor's database 430 may be distributed across one or more database servers. Similarly, while FIG. 4 illustrates only a single processor 410, it should be understood that a central monitor 120 could have multiple processors, or could be implemented using multiple computers, such as computers organized into a server cluster for purposes of providing redundancy, high availability and avoiding single points of failure. In a similar manner, the data which would be used to configure the central monitor 120 to operate in the context of the overall environment 100 (e.g., software modules 440-440n) could be stored on a single computer readable medium (such as a computer's hard disk or a removable memory element), or could be spread across multiple physical devices (e.g., a redundant array of memory elements). Different embodiments could also feature different relationships between a LIS 420 and other components illustrated in FIG. 4. For example, in some cases a central monitor 120 might have a LIS 420 integrated with its other components (e.g., the LIS 420 could be hosted by the same server(s) that execute software modules 440-440n for the central monitor 120), whereas in other cases a LIS 420 could be separate from a central monitor 120, but would interact with the monitor through a network connection. Accordingly, the discussion of a central monitor 120 set forth above in the context of FIG. 4 should be understood as being illustrative only, and should not be treated as limiting.

Figure 3:
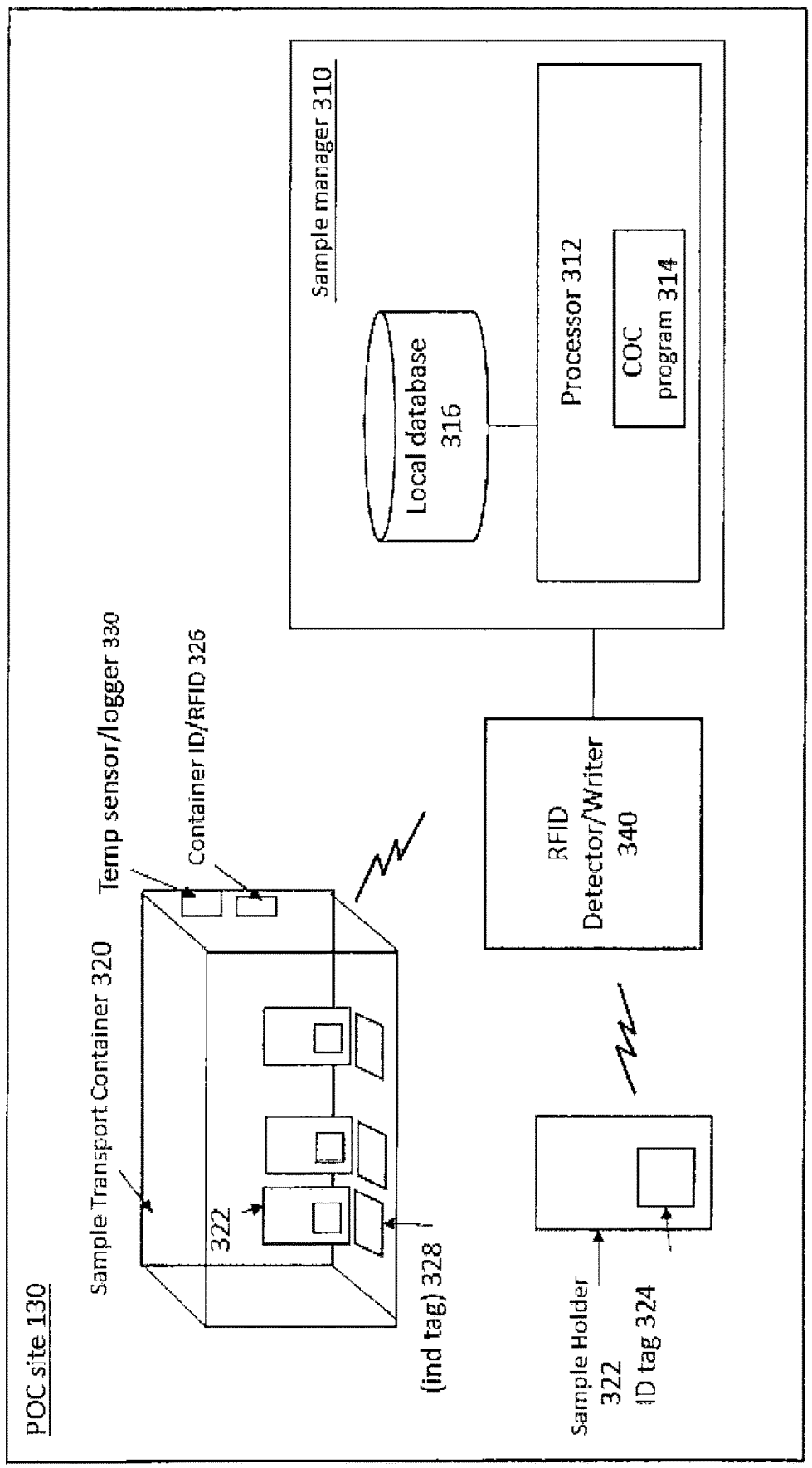
FIG. 3 is a diagram illustrating a point of collection for samples of biological material such as could be present in the environment of FIG. 1.

Turning next to the POC 130, POC 130 may be a clinic, a hospital, or laboratory where a patient sample is collected, and may include devices such as those shown in FIG. 3 to facilitate the management and tracking of those samples after they have been collected. For example, as shown in FIG. 3, a POC 130 can have a sample transport container 320 (e.g., a courier case) adapted to store and enable transport of a plurality of sample holders 322 (e.g., test tubes). Such adaptation could include, for example, the sample transport container 320 having a plurality of slots or other receptacles for sample holders 322, which slots could potentially have individual identifiers (e.g., tags 328) to help maintain consistent identification of samples while in transit even if the sample holders 322 in which those samples were placed did not have their own identifiers. Additionally, the sample transport container 320 could have its own identifier 326, and there could also be identifiers 324 for the sample holders 322 containing the individual samples, thereby potentially allowing for multiple levels of redundant tracking for detecting (and preferably avoiding) errors in the handling and treatment of samples in transit. As another example of a potential adaptation for allowing a sample transport container to store and enable transport of samples, a sample transport container could include a receptacle for a rack, so that sample holders could be placed into the rack and the rack could easily be placed securely into the sample transport container. A sample transport container 320 could also be instrumented with one or more environment sensors such as temperature sensors/loggers 330, which could be used to take measurements of the temperature of the environment inside the sample transport container 320 while samples are in transit.

In addition to items for handling, identifying and gathering relevant information about samples, a POC 130 could also include equipment for gathering and communicating information, either with other devices in the POC 130, with a remote device like a central monitor 120, or both. For example, as shown in FIG. 3, a POC can include a history logger such as sample manager 310, which could be implemented in the form of a computer comprising a processor 312, a local database 316, and a memory storing a program 314. Such a program 314 could, when executed by the processor 312, cause the sample manager to exchange information with (or send information to) the central monitor 120, associate samples with identifiers as discussed below, assist with collection or other activities for a sample, and/or perform other actions to facilitate/enable the monitoring and performance of sample handling and testing activities.

The remaining sites illustrated in the environment 100 of FIG. 1—i.e., the preparation site 140 and POT 150—could serve different roles in the handling of a sample than those described above for the POC 130, but could be integrated into the overall environment using devices which are the same as or similar to those described above for the POC 130. For example, while the preparation site 140 may be another clinic, hospital, or an intermediate laboratory for processing and preparing the collected samples for transportation, and the POT 150 may be a medical laboratory that processes and analyzes the samples, each of those sites could have a history logger or other device similar to sample manager 310, which would allow the site in which it was located to interact with the central monitor 120 and could also assist the personnel at those sites with performing their respective obligations vis-à-vis the samples. Similarly, the samples gathered at the POC site 130, processed at the preparation site 140, and tested at the POT 150 would preferably be transported between those sites using a sample transit container 320 and sample holders 322 that would move with the samples from site to site, and whose identifier(s) could be linked with the samples by both the individual sample managers 310 and the central monitor 120. In this way, even if the facilities are operating independently of one another, information on a sample may be made accessible at each of the facilities by a central monitor 120 via a network 110. For example, in some implementations of the disclosed technology, a unique sample ID may be generated and associated to each sample. Such a sample ID (which may be affixed to a container containing the sample for ease of reference by a user), along with other information such as observation notes and storage/transport information (e.g., atmospheric pressure a sample of biological material has been exposed to while in transit) may be tracked from POC site 130 to POT site 150. With this information, a healthcare provider at POT site 150 and/or a physician at a POC site 130 can be alerted when a sample does not arrive at an expected location within an interval of time or with a delay less than a time threshold for a particular test, or when the storage condition of the sample is not within a specified temperature range, exceeds a threshold or is different from the normal condition, or when any occurrence that deviates from a typical collection, transport, storage and analysis process.

Figure 2:
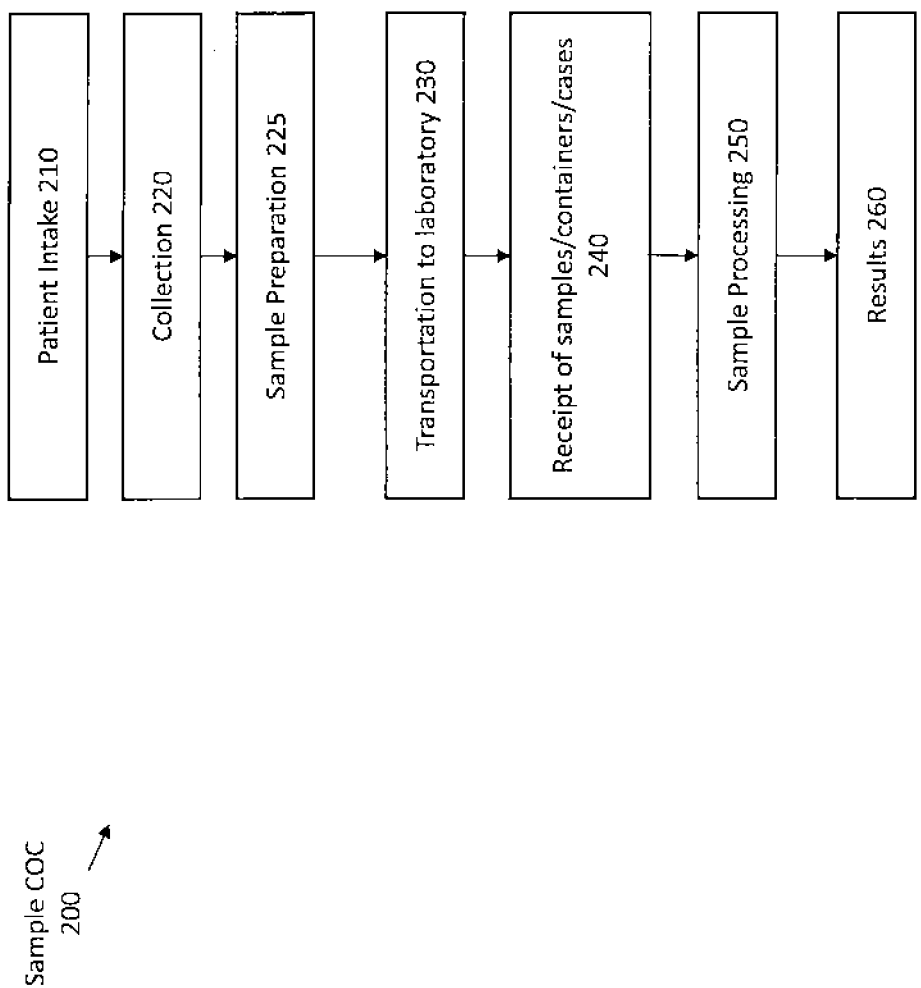
FIG. 2 is a flow chart illustrating a method for managing a biological sample within the environment of FIG. 1.

To illustrate how the disclosed technology could operate in an environment 100 such as shown in FIG. 1, consider FIG. 2, which illustrates an exemplary sample chain of custody (COC) process 200 according to one aspect of the present disclosure. COC process 200 starts at a patient intake step 210, where a patient comes to POC 130 (e.g., a laboratory or hospital) and the test(s) for that patient are determined. This test determination could take place in a variety of ways, and would preferably be facilitated through the program 314 running on the sample manager 310 at the POC 130. For example, it is possible that the patient himself or herself could have a copy of a test order, in which case he or she could simply present that order (which is often requested by the patient physician) to a custodian or a healthcare provider at the POC 130. In this type of scenario, the test order would preferably be recorded into the sample manager 310 of the POC 130, and then provided to a laboratory information system 420 (which could either be integrated with, or in communication with, a central monitor 120) for the purpose of coordinating handling of the sample throughout the environment 100. Alternatively, in some embodiments, a test order for the patient may be present in a LIS 420 prior to the patient arriving at the POC 130 (e.g., if his or her physician had transmitted the test order to the LIS 420 at the time of issuing it), in which case, once the custodian or healthcare provider at the POC 130 had entered identifying information for the patient into the sample manager 310, the sample manager 310 could send a query to the LIS 420 and the LIS 420 could respond by transmitting the test order to the local sample manager 310 (either directly, or as part of a communication link between the local sample manager 310 and the central monitor 120, depending on how those particular components were implemented in the embodiment in question). Combined approaches are also possible. For example, in some cases, LIS 420 may contain additional and updated information of a test order. For instance, a physician may order additional tests or change the number of tests for a test order after seeing the patient. In this type of scenario, after a test order was entered into the sample manager 310 at the POC 130, the sample manager 310 could query the LIS 420 for new information, and receive the updated information from the LIS 420 in response.

After the test(s) for a patient had been determined, identifiers could be generated for the sample(s) that would need to be taken for the test(s). This could be done in a variety of ways. For example, in some embodiments, after a test order had been entered/obtained from a LIS 420, a program 314 executed by the sample manager 310 could query its local database 316 for records indicating what sample(s) would need to be taken to perform the necessary test(s), and could then generate a unique identifier for each of those samples. Such a unique identifier could be generated, for example, by providing information identifying a sample (e.g., name of the patient from whom the sample is taken, test for which the sample is taken, date the test order was issued, etc.) to a cryptographic hash function (e.g., MD5, SHA-3, etc.) to generate a unique fingerprint for that sample. Alternatively, in some embodiments, it is possible that a sample manager 310 could have been issued a set of identifiers to use with its samples, and, when an identifier was needed for a sample, could query its local database 316 for the next unused identifier from its set and assign that identifier to the sample. As yet another alternative, when an identifier is needed, a sample manger 310 could send a message to the central monitor 120 requesting that the central monitor 120 provide the necessary identifier. The central monitor 120 could then respond by generating a new identifier using a cryptographic hash function, by selecting an identifier which hadn't been used by the sample manager 310 at the POC 130 (or any other sample manager, in the scenario where multiple sample managers communicate with a single central monitor), or by some other suitable method for generating the requested identifier.

Additionally, in some embodiments, once the identifier for a sample had been determined additional steps could be done to facilitate the management and handling of that sample throughout the environment 100. For example, a sample manager 310 could update its local database 316 (and send, either in real time or as part of a periodic push to or pull from the central monitor, information to the central monitor 120 instructing it to update its database 430) to show that the identifier had been assigned to the sample. This could be done by, for example, adding a database record which used the sample identifier as a primary key, and which included attributes describing the sample (e.g., the type of biological material for the sample, the patient from whom the sample was taken, the test(s) to be performed on the sample, etc.). Similarly, in some embodiments, a sample manager 310 could print a label with the identifier (e.g., encoded as a 2D or 3D bar code) which could be affixed to the sample holder 322 for the sample, or could use an RFID detector/write 340 to encode the identifier into an RFID chip in the sample holder 322. Of course, other approaches are also possible, and could be included in some embodiments as alternatives to those described above. For example, in some embodiments, rather than a sample manager 310 assigning an identifier to a sample, the individual who places the sample in a sample holder 322 could also affix a label which had been pre-printed with a unique identifier onto that holder and enter the unique identifier from that label into the sample manager 310. The sample manager could then update its database 316 (and potentially send a message to the central monitor 120 to update its database 430) with the identifier specified by the user rather than with an identifier it had itself generated. Accordingly, the discussion above of how a sample manager 310 and/or central monitor 120 could generate identifiers for samples should be understood as being illustrative only, and should not be treated as limiting.

At the collection step 220, samples are collected from the patient by a healthcare provider and each sample is placed in a corresponding sample holder 322, such as a test tube. As mentioned previously, this process could potentially be facilitated by software running on the sample manager 310. For example, a sample manager 310 could be configured to execute a program which would, after determining (or being informed, such as by a central monitor 120) what sample(s) to take from a patient, would instruct the healthcare provider at the POC 130 to take the sample, to place it into a sample holder, and to affix a label bearing the identifier for that sample (e.g., encoded in the form of a 2D or 3D barcode) onto the sample holder. Alternatively, if the sample holder 322 included an RFID tag, the sample manager 310 could instruct the healthcare provider to bring it into proximity of an RFID detector/writer 340 so that the identifier could be encoded on the RFID tag. This could offer several advantages over a printed label. For example, RFID tags can be read from a greater distance and at a faster rate than bar codes. RFID tags contain more data capabilities, can be programmed, and have high levels of security.

Additionally, for certain tests, the sample manager could provide an interface which the healthcare provider could use to add additional information for a sample, and may indicate that such information would have to be entered before collection of the sample could be deemed complete (e.g., healthcare provider may be required to enter a note in a comment field or check one or a plurality of boxes in a check list to complete the sample collection process). For example, when a special type of test is ordered, the healthcare provider may be asked to check if an adequate volume or size of the sample is obtained. Similarly, the healthcare provider may be asked to indicate the sample volume on the label or enter it into a local sample manager 310 which would then associate it with an identifier for that sample so that the volume could be used to ensure that the sample was handled properly at a subsequent preparation site 140, POT 150, or both (e.g., if the sample is a blood sample, the volume of the sample could be used to account for the necessary anti-coagulant when preparing a dilution, thereby reducing the risk of a test performed on the sample providing incorrect results). In one embodiment, the COC program 314 might be written so that the healthcare provider could not close it or perform further actions for that sample (or any other sample) if the comment field is not filled out or if none of the boxes are checked. A COC program 314 may also encode such information (or other additional information) along with the identifier for a sample on a sample holder. For example, if an identifier for a sample is encoded into an RFID on a sample holder, the RFID could also be encoded with information such as patient identification information, container information, a description of the collected sample, tests to be run on the sample, the test order to which the sample relates, and conditions of the patient at the time the sample was collected (similar information could also be included on a label printed by the sample manager 320 to be affixed to a sample holder). The COC program 314 may also require the healthcare provider to scan his or her ID before exiting the COC program 314. This could prompt the COC program 314 to record the date, time, location and the healthcare provider associated with the sample collection process. Alternatively, in embodiments where a healthcare provider is required to log in to use the sample manager 310, the COC program 314 may record the login credential of the healthcare provider and associate it with sample collection date, time, location, etc.

Samples collected at collection step 220 may be sent to a sample preparation site 140 at step 225, where the quality of the samples, such as volume or liquid level and sedimentation, may be interrogated. Preparation site 140 may also further process the collected samples such as by performing (additional) preparation activities as necessary or as required by the test order. For example, if a particular test requires blood samples to be separated by component, the blood samples may be centrifuged at the preparation site 140. Once the blood samples are separated into different components via centrifugation, each of the components may be placed in a separate container. In another example, a laboratory technician may check the required volume for a particular test. If the volume of the collected sample is not adequate for a particular test, the sample may be sent back for additional sample collection. U.S. published patent application number US2013/0123089 describes various systems and methods for liquid volume or liquid level detection within a container. The disclosed methods and systems are incorporated herein by reference.

Volume of a sample may be tested using a level detection unit, which may comprise a camera unit and image analysis software. The level detection unit measures the sample's volume or liquid level by capturing and analyzing one or more images of the container and the liquid/sample therein. The camera unit may be a still camera, a color image camera, a video camera, a spectral camera or the like. The settings of the color camera, such as focusing, white balance, diaphragm setting, filling-in, can be permanently preset or adjustable. The settings can be adjusted with the aid of image evaluation software. An algorithm can be used to calculate the sample level and/or volume using known data, such as the type of sample tube used, the type of sample, etc.

Alternatively, the liquid level detection unit may employ laser diodes, with a defined wavelength range, to evaluate the absorption spectra. A laser diode beam can be focused on sections of a container, and an absorption and transmission measurements of different wavelengths of the focused beam can be measured to determine the liquid level and volume.

As with sample collection 220, this sample preparation can also be facilitated using a sample manager 310. For example, a sample manager 310 located at a preparation site 140 could present an interface which would allow a user to enter an ID for a sample (or could allow a user to provide the sample's ID in an automated manner, such as by scanning a bar code or reading an RFID tag) and, once the ID of a sample had been provided, could use that ID to query the central monitor 120 for information on how that sample should be processed. The sample manager 310 could then use that information to inform the personnel at the processing site 140 what to do with the sample. The sample manager 310 could also inform personnel at the processing site 140 of any problems that might exist with a sample. For instance, the sample manager 310 (or the central monitor 120) could compare elapsed time between when a sample was taken and when it arrived at a processing site 140 (i.e., the duration of time the sample of biological material was in transit) with stored information indicating how much time could elapse before a particular type of sample was no longer suitable for processing, and this information could be used to inform personnel at the processing site if the processing they would otherwise have performed was no longer appropriate. Similarly, the sample manager 310 (or central monitor 120) could compare information on the temperature of the sample's environment gathered by sensors in the sample transport container with stored information indicating acceptable and unacceptable temperature ranges/acceptable temperature thresholds, and the results of such a comparison could be used to inform personnel at the processing site if the processing they would otherwise have performed was no longer appropriate. Additionally (or alternatively), a sample manager 310 could ensure that personnel at the processing site 140 had provided appropriate information about the samples they worked with. For instance, just as a sample manager 310 at a POC site 130 could require personnel at the POC 130 to enter various information before sample collection would be deemed complete, when a quality check for liquid levels and the sample separation process are completed, a sample manager 310 at a preparation site 140 may require a healthcare provider to scan the sample and enter any observation in a comment field, or alternatively select and check off boxes such as centrifugation completed, volume and visual check completed, etc. on a list provided by COC program 314.

At step 230 sample holders 322 may be placed in a sample transport container 320 and sent to POT site 150 such as a laboratory. Sample transport container 320 may be affixed with various environmental sensors for monitoring temperature (i.e., temperature sensors), pressure (i.e., pressure sensors), altitude, and the like. In some embodiments, the transport container 320 and/or individual sample holders 322 may be affixed with a GPS device for location tracking. In certain cases, it may be important to affix a GPS device to each individual sample holder 322 in order to accurately track the location and transit route of each sample holder 322 since holders in a single transport container 320 may be separated.

At step 240, transit data are collected when courier case 320 arrives at POT site 150. The types of data collected may be any information relating to the sample collected during transit including (but not limited to): total travel time; time of travel initiation; temperature exposure profile; elevation; number of stops; locations (GPS data); pressure; courier information, etc. For simplicity, these types of data will be referred to as 'transit data'.

Transit data may be collected manually or automatically. In one aspect, step 240 may require a technician at POT site 150 to scan the sample transport container 320 to indicate the receipt of the container 320 and the samples contained therein. Each of the sample holders 322 within the transport container 320 may also be read (e.g., using a bar code scanner, if they are tagged with bar codes). The technician may also be required to scan various sensors (e.g., temperature, GPS, elevation, etc.) affixed to the sample transport container 320 and/or the sample holders 322. Once the sensors are scanned, the collected data will be entered into a sample manager 310 at the POT 150, and will preferably be stored in both the local database 316 of that sample manager 310 and the database 430 of the central monitor 120 in records which are directly or indirectly associated with the sample(s) that were delivered. This data could then be compared to parameters for a medical diagnostic test for the relevant sample, such as temperature, pressure, or other thresholds which could indicate if some type of special processing for the sample was necessary.

It should be noted that each of the sensors (e.g., temperature, atmospheric pressure, GPS, elevation, etc.) may collect and store data at many intervals during the transit of a sample. For example, a temperature sensor may start collecting temperature data immediately after the sample preparation stage 225 or at step 230 and may not stop collecting data until scanned and/or stopped at step 240. Accordingly, a temperature sensor may collect and store a complete temperature profile of a sample for the entire transit showing the temperature the sample had been exposed to while in transit. Likewise, a GPS sensor may collect and store a complete location profile of a sample to show when and where the sample been at any point during the transit. Once scanned, the sensor may be configured to automatically stop collecting data. Alternatively, the sensor may be configured to collect and store data until it is stopped by a custodian.

Transit data may also be collected automatically using RFID tags affixed to sample holder(s) 322 and/or a sample transport container 320. In this way, transit data from sensors may be automatically retrieved by a RFID detector/writer 340 (FIG. 3). It should be noted that each RFID tag may be coupled to a plurality of sensors, in which case the RFID would preferably be programmed to provide data from any of the sensors selectively when interrogated by a device such as an RFID detector/writer 340 connected to a sample manager 310. Alternatively, each sensor may have its own embedded RFID tag that enables it to be read and/or programmed. Two or more sensors may also be communicatively linked to each other. In one aspect, a single sensor may be used to collect all of the transit data.

Of course, it should be understood that the discussion above of collecting transit data once a sample transport container 320 arrives at a POT 150 is intended to be illustrative only, and that in some embodiments (including embodiments which support collection of transit data at a POT 150) transit data may also be collected remotely at any time during steps 230 and 240 by coupling one or more sensors to network 110 via a gateway (e.g., a cellular transceiver built into, or proximate to, a sample transport container 320), which may employ various wireless communication protocols such as satellite communication, mobile communication, etc., to connect with network 110. Each of the sensors may be connected to the gateway using RFID communication, WiFi, near field communication (NFC), Bluetooth communication, etc. In this way, transit data may be collected by a sample manager 310 or central monitor 120 at any time.

Quality checking may also be performed at step 240. For example, each sample within the sample holder(s) 322 may undergo testing if any of the transit data (e.g., temperature profile, transit time, pressure profile, etc.) of the sample holder 322 (or, in the case of data which might be available from a sensor on a transport container 320 but not from the sample holder(s) 322 it contains, transit data from the transport container 320) falls outside a predetermined range or specified condition. Samples may be marked as non-conforming any of the transit data profiles fall outside of an acceptable range. Additionally, a sample manager 310 could provide instructions to the personnel at a POT 150 indicating how the non-conformity should be addressed. For example, in some cases, a non-conformity could be severe enough relative to the requirements of a particular test that the non-conformity would prevent the test from being done (e.g., if a blood sample was simply too small to allow it to be tested, or if it had been delayed so long in transit that it would have coagulated, etc.), and the sample manager 310 could indicate to the personnel at the POT 150 that they should discard the sample and/or that they should request that another sample be collected to perform the medical diagnostic test. Alternatively, in some cases a non-conformity, rather than preventing a test from being done at all, could change the how the test should be performed or interpreted. For example, it is possible that a meaningful result could still be obtained if the test was rerun one or more times, or if the results of the test were interpreted differently than if there hadn't been a non-conformity (e.g., using a modified evaluation parameter, such as if a lower level of a test product would be considered a positive result than would have been the case had there been no non-conformity). In such a case, a sample manager 310 could provide instructions to the personnel at the POT 150 indicating how they should adjust their interpretation or performance of a test result to accommodate the non-conforming sample(s).

Once the samples are processed at step 250 and the results are passed on to the healthcare provider who ordered the test, the patient, a laboratory manager, or LIS 420 at step 260.

In one aspect, each of steps 210, 220, 225, 230, 240, and 250 may require a health care provider to indicate that one or more actions required by each respective step have been completed using COC program 314. This may be done by exiting the COC program, clicking on a complete button, saving the COC program, or by other means as provided by COC program 314. A health care provider may also be required to enter/scan his or her ID or otherwise establish his or her identity, such as by entering a name and password combination to access a sample manager. Similarly, in some embodiments, health care providers may be required to indicate completion of steps either in addition to, or as alternatives to, those depicted in FIG. 2. For example, in some embodiments, a COC program might require a health care provider to indicate that a sample had been placed into storage after processing 250 of that sample was complete, and/or to indicate that the sample had been disposed of after it was no longer needed/suitable for further testing. In this way, COC program 314 may record relevant data such as date, time, and location of the completed action along with the healthcare provider ID.

In one embodiment, COC process 200 may include a process for checking the status of a sample and/or for obtaining any information related to the sample such as its transit data. Status information may include information relating to testing progress, test results, transit status, etc. As mentioned above, transit data may be any information relating to the sample collected during transit such as: total travel time; temperature exposure profile; elevation; number of stops; locations (GPS data); pressure; courier information, etc. In some embodiments, at any step in COC process 200 (i.e., steps 210 through 260), a user may check the status of a sample and/or obtain transit data of the sample via central monitor 120. This may be done by providing the test order number or container ID to central monitor 120.

However, even in embodiments where all information for a particular sample is theoretically available, controls may be in place so that not everyone will be able to view all of the data available for a particular sample. In one aspect, central monitor 120 may restrict information access based on a user's credential. For example, couriers and lab personnel may have a low level access credential. Whereas, physicians and patients may have a high level access credential. Information that can be queried and retrieved (e.g., status and transit data) from central monitor 120 may be collectively referred to as logging or tracking information. The amount of such information a user can obtain may be based on the level of access credential. In other words, different amounts or levels of information may be provided to different users, such as patients, couriers, or healthcare providers in order to provide different level of data access.

For instance, when a user is a physician, the provided information may include testing progress/status information, test results, patient information, sample ID, container ID, courier case ID, and the chain of custody information. When the user is a courier, for example, the information the courier is able to retrieve may be limited in order to protect patient privacy. As such, the information retrievable by a courier may include sample ID, container ID, testing status information, and the chain of custody information.

Figure 5:
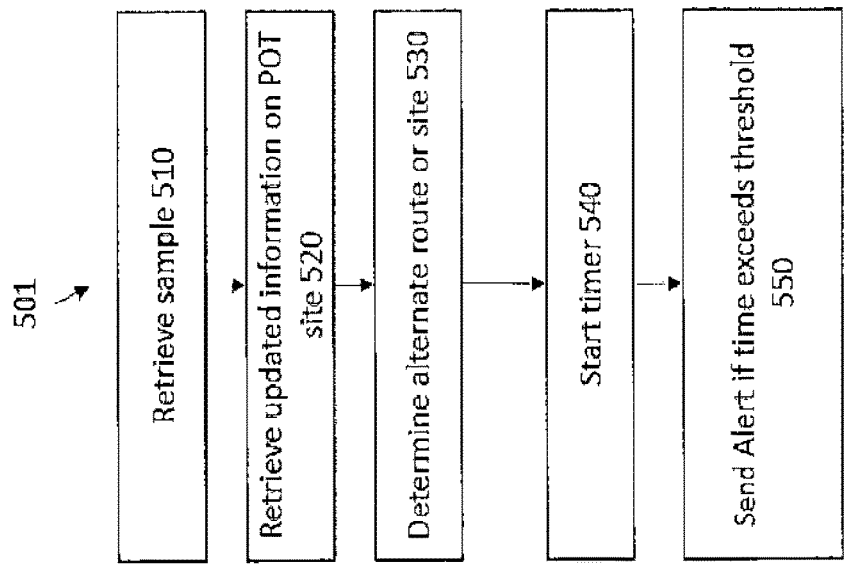
FIG. 5 is a flow chart illustrating another method for managing a biological sample in accordance with one embodiment of the present disclosure.

As a further illustration of how the disclosed technology could potentially be used in practice, consider FIG. 5, which illustrates a sample management process 501 according to one aspect of the present disclosure. Process 501 starts at step 510 where sample transport container(s) 320 or sample holder(s) 322 are picked up (e.g., from a preparation site 140, or from a POC site 130 if no intermediate preparation is necessary or the POC site 130 and preparation site 140 are the same) for transport to a POT 150 (which, in a case where there are multiple POTs, could be a predetermined POT, or a POT which is determined dynamically as described below).

At step 520, updated information on various POT sites is retrieved. In this way, the availability of a POT site can be confirmed by accessing information from central monitor 120. For example, there may be a long turn-around time at the default POT site because of a large volume of tests, or an instrument for a particular test analysis is down for maintenance. In this instance, while an alternative POT site may be farther away, the alternative POT site can service the test orders in a shorter amount of time due to availability. In embodiments where this type of availability confirmation functionality is provided, the sample managers 310 at the various POTs to which samples could be taken could be configured to constantly provide information relating POT site availability, instrument health, test volumes, etc. to the central monitor 120. As such, availability of a POT site or availability of other laboratories within the vicinity and the like are routinely updated and may be readily retrieved.

Route assisted service may be utilized at step 530. For example, an alternative POT site may be identified at step 520 and the courier may not be familiar with the route or location of the alternative POT site. In this type of scenario, the courier could send a request to the central monitor 120 for route assistance, and the central monitor 120 could respond with the best route or alternative routes to get to the desired POT site, either using pathfinding software built incorporated into its own local programming, or an API to a third party provider of route information (e.g., Google). As another example, there may be two high priority containers, each containing a sample which requires testing within a specific time period and at a specific location. In such a case, instead of choosing the shortest route between the two locations, the courier may employ the route assistance functionality provided by a central monitor 120 to aid in the decision making process. For example, the central monitor 120 could use its information on the priority of the containers and the time period during which the samples within those containers would have to be tested to determine that speed of transport should take priority over minimizing distance, and could then take different factors into account such as traffic conditions, urgency of the respective samples, etc. to determine the best route. In this way, urgent samples can be delivered on time and meet delivery performance requirements. Other information could also potentially be considered by a route assistance feature. For example, in some embodiments, the availability of reimbursement from an insurance company for testing performed at different facilities might be considered in deciding which facility a particular sample should be taken to.

As mentioned previously, in some embodiments, route assistance functionality may be provided by a program executed by the central monitor 120. Such a program could use information provided to the central monitor 120 regarding the operational status and health of each instrument at the potential POTs periodically or in real time. This information can then then be stored in database 430 and run against a set of rules specifying actions to take when certain defined criteria are met. In embodiments where they are present, such rules could potentially also be stored in the database 430 of the central monitor 120, or could, alternatively or additionally, be stored in the LIS 420.

In one embodiment, a program 440 executed by the central monitor 120 could evaluate rules relating to dynamic scheduling, that is, the capability to dynamically adjust routes based the availability of different POT sites and the instrument health at each site. Dynamic scheduling may also relate to the capability of rescheduling via air or ground transport between different couriers based on the load of POT sites and urgency of the samples. A rule engine within a central monitor 120 checks the rules in database 430 for tests required and availability status of the instrument to identify an appropriate POT site for testing a sample. In one embodiment, a default laboratory with various analyzers may be assigned to a particular POC site 130. When the default laboratory is unavailable, the central monitor 120 could, either automatically upon determining that the default laboratory is unavailable or in response to a request for route assistance from a courier, at step 530 may invoke a set of rules to find the next POT site with the shortest route, shortest time of travel from the POC site, or the shortest estimated time to complete the test based on the above mentioned factors.

In one embodiment, a central monitor 120 stores a timestamp to indicate the date and time when each sample holder is received at or shipped to a location between collection and testing. A timer may be started within central monitor 120 when a RFID tag of a given container is read at a location at step 540. When an expected time period is exceeded and the sample has not arrived at the expected location, an alert may be generated at step 550. In some embodiments, a sample transport container 320 may be instrumented with a GPS device, and when the container passes a predetermined POT site, a flag may be generated. The flag may be delivered to the courier who is last in a chain of custody or a laboratory manager at the POC site or a laboratory manager at the POT site via email, page, text message, voice message, or other means.

At POT site 150, when a sample transport container 320 is delivered, the ID of that container 326 can be obtained to identify the content of the container. Container ID 326 can be scanned by a scanner if the container ID is a 2D or 3D barcode. If container ID 326 is an RFID tag, it can be read by a wireless reader or a wired reader connected to the sample manager 310. The technician at the POT site may unpack the sample transport containers, verify that the samples are all in a good condition and that the temperature in the containers has always been below a certain limit. If it is not the case, as an alternative (or supplement) to the automatic detection of non-conformities described previously, the technician may declare non-conformities for a sample or a set of samples in the product. The technician may also add comments and observations on the samples and/or to local database 316 via the sample manager 310 at the POT. The information may also be transmitted to central monitor 120. If the samples are confirmed, the technician may declare that the samples in the container have been received and will be processed for testing.

In some embodiments, a custodian chain of custody is monitored and kept track of between collection and testing of a sample. When such a chain of custody is instituted, each custodian who collects a sample, prepares the sample, transports the sample, performs analysis on the sample, or handles the sample in anyway may be required to register within a local sample manager 310 or central monitor 120. Each custodian may register/authenticate his or her identity by manually entering his or her identification information (e.g., user name and password) or by having an identity token read by the system (e.g., having an identification badge with an embedded RFID tag scanned). Alternatively, a custodian may be verified and logged into the system using biometric authentication, which may be performed by a biometric reader such as a finger scanner, palm scanner, eye scanner, facial scanner, or speech analyzer.

In one embodiment, where a biometric reader is used to determine identity, the biometric reader may be a finger scanner that is available via a mobile app and which would operate using capacitive touch technology provided by the device running the app. Non-limiting biometric technology of this type includes Touch ID™ detector in Apple's iPhone™ and iPad™ products for example. A mobile app is a computer program or software module designed to run on mobile devices such as smartphones, tablet computers, and the like. As each sample is handed off from one provider to another, each provider may be required to have his or her finger scanned by a mobile device, and the software running on that mobile device might then send the scanned fingerprint information to the database 430 of the central monitor 120 for storage and to assist the central monitor 120 with establishing a chain of custody. In this way, the entire record including timestamp of providers having custody of the sample may be recorded and tracked.

In some embodiments, a biometric reading of a patient at the patient intake step 220 is obtained in lieu of interviewing the patient to get the patient information, and such biometric information for the patient may be stored in the database 430 of the central monitor 120 and associated with the samples taken from that patient in a manner similar to that described previously.

Figure 6:
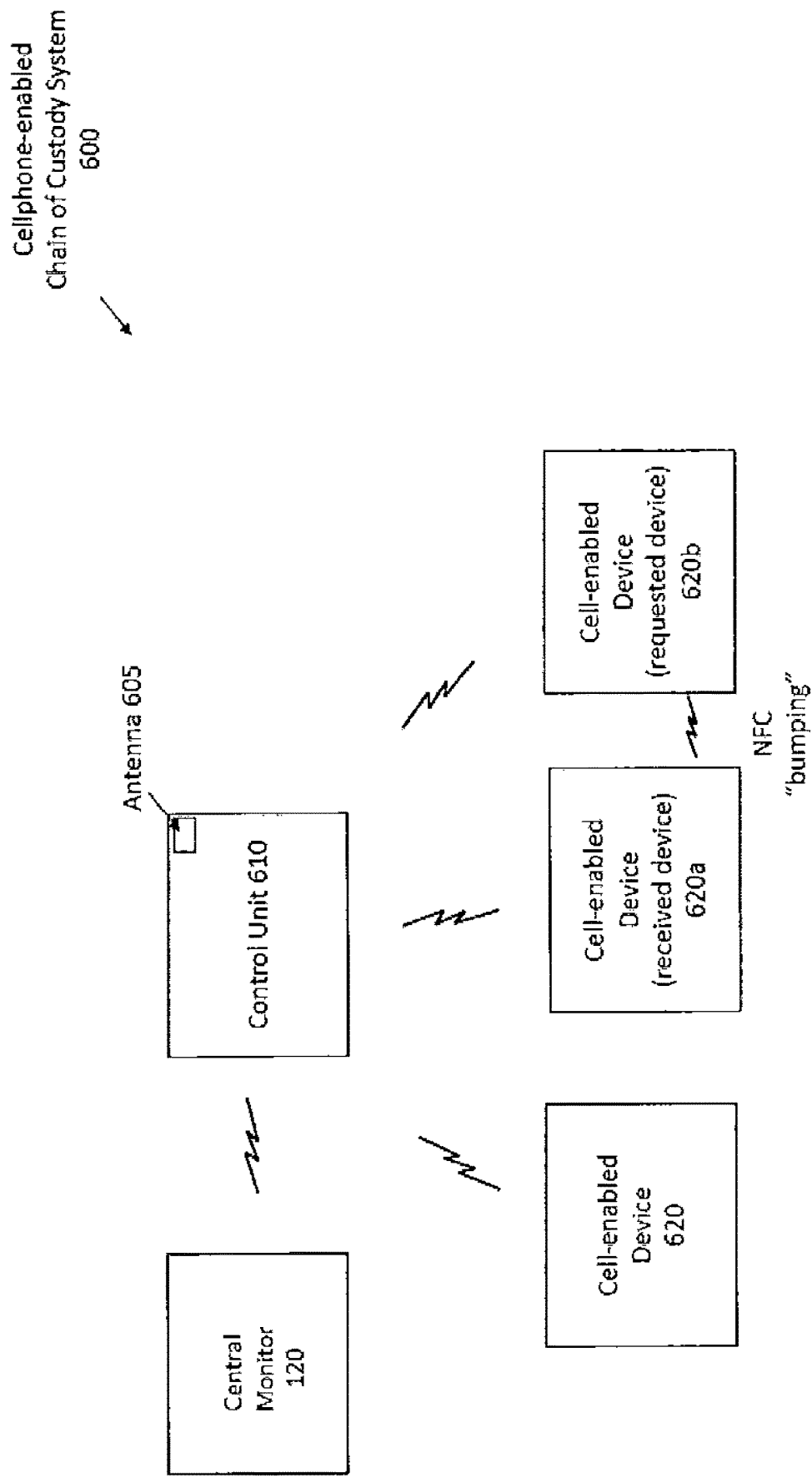
FIG. 6 is a diagram illustrating a chain of custody system in accordance with one embodiment of the present disclosure.

To further illustrate how the disclosed technology could allow a central monitor 120 to use devices beyond sample managers at a POC site 130, processing site 140 and POT 150, consider FIG. 6. That figure illustrates a cellphone-enabled chain of custody (COC) system 600 operating within the environment 100 of FIG. 1 according to one aspect of the present disclosure. Cellphone enabled COC system 600 includes a control unit 610 equipped with an antenna 605 for receiving data from mobile history loggers such as devices 620*a-n*, which could communicate wirelessly with other components of the system using hardware such as wireless transceivers or wireless receiver/wireless transmitter pairs. Control unit 610 is configured to communicate with central monitor 120 through wireless or wired communication protocols. Devices 620 may be cellphone-enabled devices that are capable of communicating with the control unit 610 via a cellular network. While in some embodiments cell enabled devices could potentially communicate directly with the central monitor, preferably such communications will be funneled through a control unit 610, as this would enable the central monitor 120 to limit its communications to a relatively small number of trusted devices (i.e., the control unit 610 and the sample managers 320). Devices 620 could include, but are not limited to, cellphones, mobile devices, laptop computers, or any other devices that are capable of communicating with control unit 610 via a cellular communication network, satellite network, or plain old telephone service, etc.

In some embodiments, devices 620 are equipped with local communication technology such as Wi-Fi, Bluetooth™, or near filed communication (NFC) technology. Devices such as smart phones often contain unique identifiers along with GPS applications, which allow them to function as locator devices within a cellular/GPS network. In a cellphone-enabled COC environment, each healthcare provider and/or courier could be provided with cellphone-enabled device 620 or could be required to download software configured to communicate with a control unit 610 (or central monitor 120) on a mobile device he or she already possessed.

In one embodiment, rather than relying on sample managers at the POC 130, processing site 140 and POT 150, each healthcare provider could be required to activate a COC app whenever handling a sample. This could entail both running the application on the provider's device, and using a biometric sensor within device 620 to verify and register the provider's identity. The registered identity along with other information associated with the provider, such as name, date of birth, unique ID number, gender, photo, biometric profile, qualification, and certifications, may be sent to control unit 610. The information from control unit 610 is then sent to central monitor 120 where the information can be stored and further distributed to other cell-enabled devices or sample managers 320 as appropriate.

In addition to communicating via a central monitor 120 and/or control unit 610, in some embodiments devices in an environment 100 such as shown in FIG. 1 could be adapted to detect and communicate with each other devices (e.g., devices 620*a* and 620*b*) via local communication technology without requiring intermediation by other devices. For example, in some embodiments, as a sample transport container 320 is handed off from one provider/courier to another, the "bumping" of devices carried by the individual involved in the hand off could capture information of the provider identities and the time when the exchange of the container 320 takes place.

Figure 7:
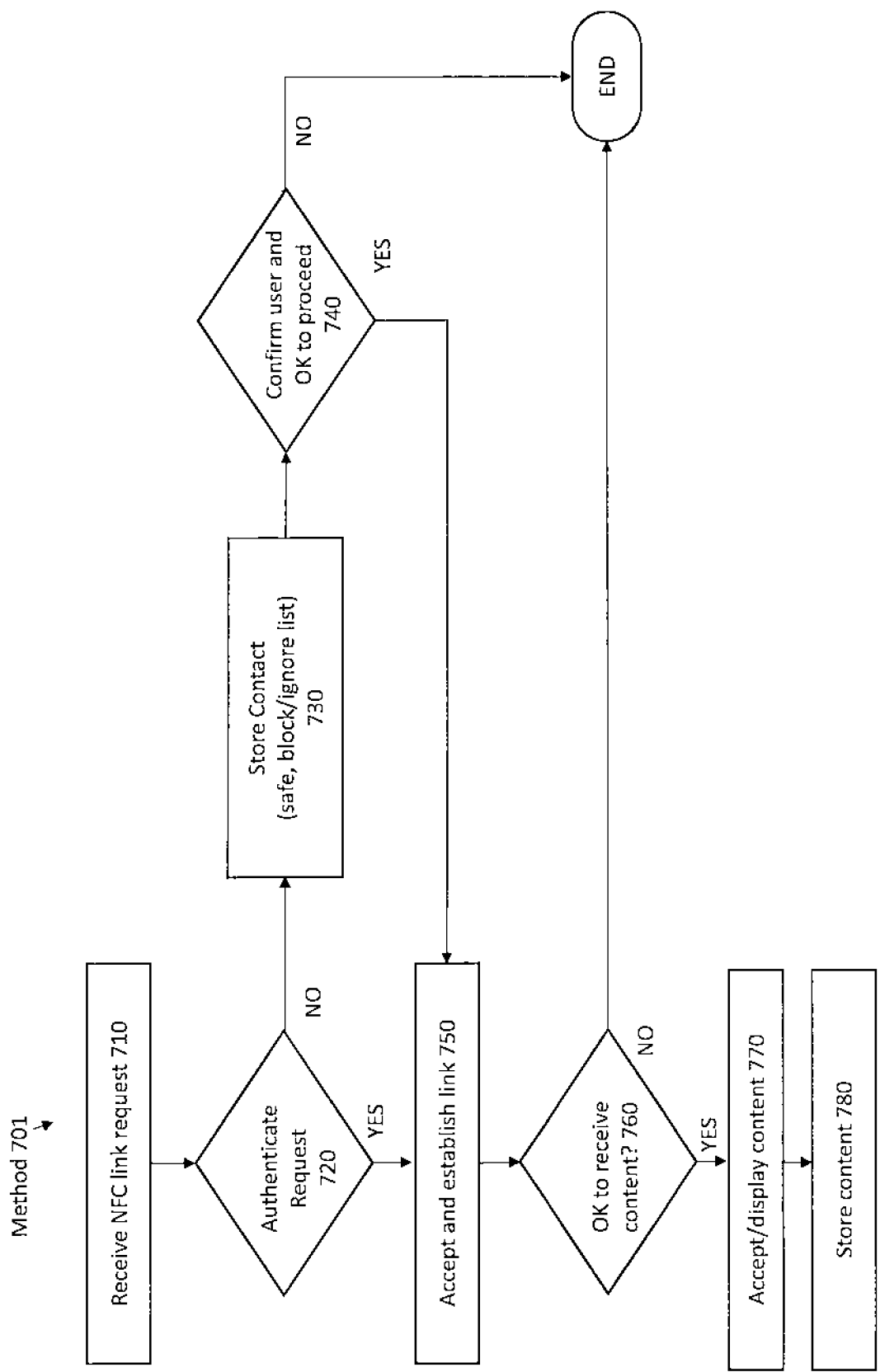
FIG. 7 is a flow chart illustrating a method for adding and sharing information within a near field communication (NFC) share group in accordance with one embodiment of the present disclosure.

FIG. 7 illustrates a flow diagram of a method 700 for sharing and "bumping" of information between devices 620*a* and 620*b* of FIG. 6. Device 620*b* is a device that initiates a NFC connection/link and a content transfer request. Device 620*a* is a device that receives the request. Whenever registered devices 620*a* and 620*b* are in close proximity of one another, an alert may be raised so contents of the devices may be shared using near field communication. Method 700 begins at step 710, when the receiving device 620a receives a request to establish a communication link. The request contains an identifier, which may be an identifier assigned to the device for the purpose of tracking its operation in the relevant environment 100 (e.g., by a central monitor 120), or could be a unique identifier which is intrinsic to the requesting device 620b itself (e.g., an ISMI number from a SIM card included in the requesting device 620b). The received request may optionally include communications or other parameters for facilitating the establishment of a NFC communication link between devices 620a and 620b. In order to receive and process the link request, each device may have an NFC app running on a processor to monitor received near field communications for incoming requests. Alternatively, each device may have a special installed app that automatically detects other registered devices when they are in near field communication.

At step 720, the request for data exchange via NFC is authenticated. In deciding whether or not to accept the request, the user of device 620a (or software executed by or at the request of device 620a) may compare the received identifier (device identifier) with a list of authorized identifiers or a list of block identifiers. If the device identifier is on the list of authorized devices, the request may be automatically accepted. Conversely, if the device identifier is on a block list, the request may be ignored and the link will not be established. However, if a match cannot be located on either list, a message may appear at both devices to terminate the NFC app or request the user of device 620b to resend the identity for verification/addition to the block or authorized lists as appropriate. In this exemplary embodiment, the list of authorized device identifiers may be available through the NFC app or from a predetermined list stored in memory of device 620a. Alternatively, a list of approved device identifiers may be stored on central monitor 120.

A device identifier used for authentication, as described above, may be one or more data points relating to a device. For example, a device identifier may include one or more of an NFC identifier, a Media Access Control MAC address, and name of the user associated with device 620b. Device identifier may also include the user physical addresses, phone numbers, email, job function, or any information associated with device 620b. The device identifier may be unique to each device, to each user, or may be unique to the user and device combination. For example, user A and user B will each have a different device identifier even though they may be using the same device (i.e., device 620b). Alternatively, in some embodiments the device identifier for device 620b may remain the same regardless of the user.

If the authentication fails at step 720, the device identifier of device 620b may be stored at step 730 so that it could later be added to the safe or block list as appropriate. In one embodiment, the device identifier of device 620b will automatically be added to the block/ignore list if it is not on a safe list at the time the request for content transfer is received. Alternatively, in some embodiments, device 620b may be added to the authorized list upon user confirmation by the user of device 620a at step 740. If confirmed at step 740, the process proceeds to step 750 where a communication link is established. Conversely, if device 620b is automatically or manually added to the block list, the process ends.

Once a near field communication link is established between devices 620a and 620b at step 750, information can be exchanged between the devices over the communication link.

In one embodiment, once approved by the user at step 740, the device identifier (device 620b) may be added to a NFC or share group. Using various information (e.g., job title, function, etc.), which in some embodiments might be embedded in or used for (and could potentially be extracted from) the device identifier, and which in other embodiments might be requested from the device 620b after the communication link was established, device 620b may be automatically associated with a group of similar users. For instance, if a device identifier of a new device is associated with lab technician or a courier, then the device identifier of the new device may be automatically associated with a corresponding share group with other individuals identified as being (or devices identified as being associated with) a lab technician or a courier.

At step 760, after the communication link is established, a message at the receiving device 620a may appear asking the user to permit a file transfer or display. If the user of the device 620a selects "no" the process ends. Otherwise, the content may be transferred, and/or displayed on device 620a at step 770. The content may also or alternatively be saved locally on device 620a in its memory at step 780. Different information may be transferred under different situations. In one embodiment, only COC information such as a time-stamp when the transfer occurred and identity of devices 620a and 620b are transmitted. Alternatively, in some embodiments, users of devices 620a and 620b may belong to different health care networks which do not share a central monitor 120. In this situation, the entire content of the sample and COC information may be transmitted to device 620b via the established NFC link. Essentially, this would allow the exchange of information between devices during transfer of the sample to replace the database of a central monitor in the same manner that a blockchain of a virtual currency would allow the distributed processing performed by users of the virtual currency to replace a central database managed by an issuing authority. In other embodiments, a web link, a URL or an address of the location from which the content can be retrieved is sent.

Software which performed a method 701 such as shown in FIG. 7 may further log every action and decision taken in each of the steps 710 through 750. For example, all link and file transfer requests, whether allowed or denied, may be recorded in a log file which may be stored within the device(s) which participated in the method. The log file may be also sent to the control unit 610, and in turn can further be pushed to or pulled by the central monitor 120.

As a further illustration of how this type of near field communication data exchange could be used in the context of the disclosed technology, consider FIG. 8, which describes an exemplary method 801 illustrating the sharing of COC information (e.g., transit data) using NFC communication. In one scenario, a courier picks up a sample transport container 320 at POC 130 for delivery to POT 150. The courier carries along his personal standard issued courier device 620b, which is used to log COC information such as the courier ID and the time the courier picks up container 320. At step 810, the courier registers his device with a COC program 314 running on a sample manager 310 and initiates a NFC link (or bumping) in a manner described above with device 620a, which may be a handheld device issued to a laboratory phlebotomist.

At step 820, as soon as the COC information is registered with COC program 314, container 320 information along with container ID and other information are also correlated and associated with the COC information within COC program 314. Similarly, the courier can initiate another NFC link upon arrival at POT site 150. In this way, COC program 314 can be provided with information as to when container 320 was picked up at POC site 130 and arrived at POT site 150 and the identification of people who have handled container 320 and/or how many individuals have handled the sample of biological material while in transit. At step 830, tracking information such as COC information, and testing status of samples in container may be provided to a user.

In another scenario, the courier carries along a courier device 620b that is configured to scan shipping packages, including sample transport container 320. The courier may use device 620b to scan sample transport container 320 by reading the bar code that may be affixed to the case. Alternatively, sample transport container 320 may have an RFID tag that could automatically be read by an RFID reader at a facility. In one aspect, device 620b is also configured to read RFID tags.

Once sample transport container 320 is scanned by device 620b (when the case is picked up at POC 130), device 620b may send a pick up confirmation to control unit 610 and/or to central monitor 120. Device 620b may be in continuous communication with sample transport container 320 for the entire duration of shipping period (i.e., from POC 130 to POT 150). In this way, device 620b may regularly collect transit data (e.g., location, temperature, travel time, etc.) from sample transport container 320 through the duration of the shipping period. Device 620b may also send the collected transit data to control unit 610 at any time during the shipment period. This may be done intermittently (automatically) or on demand, at the user request via control unit 610. Finally, once sample transport container 320 arrives at POT 150, device 620b or receiving device 620a may send a receipt notification to central monitor 120.

In one aspect, device 620b may also send a notification to a COC subscriber or a share group indicating that the sample has arrived at the testing site. The notification may be sent via a mobile messaging service or via email.

Similar to the manners described above, the notification message may include the content of COC information and the test result conducted at POT site 150, or information about the content such as a link, URL, or address of a location from which the content can be retrieved. The notification may alternatively or additionally cause a notification to be displayed on each device of an option to download the content to the device.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

As used herein, the singular forms "a", "an", and "the" include plural referents unless the context clearly dictates otherwise. The invention has now been described in detail for the purposes of clarity and understanding. However, it will be appreciated that certain changes and modifications may be practice within the scope of the appended claims.

As used herein the term "patient" refers to a human or non-human subject who is being tested, treated, monitored or the like for a medical condition, disease or the like by a custodian.

As used herein, the term "custodian" refers to any person who handles, carries, or performs a test, a diagnosis test specifically on, a sample. The term is most often associated with a carrier, a courier, a phlebotomist, a laboratory technician, a laboratory manager, and any employee, affiliate, colleague or agent of an organization associated with laboratory, hospital, medical clinical or a physician office. In some cases, the term custodian also includes a healthcare provider as defined below.

As used herein, the term "healthcare provider" refers to a patient's care provider who is associated with laboratory, hospital, medical clinical or a physician office. The care provider is typically associated with ordering a test on a patient sample for disease diagnosis and/or providing care or treatment to the patient. The term is most often associated with a primary care physician, a nurse, or a nursing assistant, a pharmacist, any employee, affiliate, colleague or agent of the aforementioned organizations.

As used herein, the term "machine" refers to a device or combination of devices.

As used herein, the term "network" refers to any collection of networks using standard protocols. For example, the term includes a collection of interconnected (public and/or private) networks that are linked together by a set of standard protocols (such as TCP/IP, HTTP, etc.) to form a global, distributed network. The term is also intended to encompass variations that may be made in the future, including changes and additions to existing standard protocols or integration with other media (e.g., television, radio, etc).

As used herein, the term "sample" refers to any biological sample, and the phrase "biological sample" is meant to cover any specimen of biological material which has been isolated from its natural environment, such as the body of an animal or a human being. It can be in solid form such as tissues, bones, ligaments, and the like. It can also be in liquid form such as blood, spinal fluid, and the like.

As used herein, the term "set" refers to a number, group, or combination of zero or more things of similar nature, design, or function.

As used herein, the term "based on" means that something is determined at least in part by the thing that it is indicated as being "based on." To indicate that something must be completely determined based on something else, it would be described as being based "exclusively" on whatever it is completely determined by.

As used herein, modifiers such as "first," "second," and so forth are simply labels used to improve readability, and are not intended to imply any temporal or substantive difference between the items they modify. For example, referring to items as a "first program" and a "second program" in the claims should not be understood to indicate that the "first program" is created first, or that the two programs would necessarily cause different things to happen when executed by a computer. Similarly, when used in the claims, the words "computer" and "server" should be understood as being synonyms, with the different terms used to enhance the readability of the claims and not to imply any physical or functional difference between items referred to using those different terms.

The invention claimed is:
1. A machine comprising:
a) a sample transport container, the sample transport container adapted to store and enable transport of a plurality of sample holders for samples of biological materials collected from patients;
b) a set of one or more environment sensors adapted to take measurements of one or more characteristics of an environment of the sample transport container;
c) a set of one or more history loggers, wherein each history logger from the set of history loggers is programmed to receive transit data for those samples of biological material; and
d) a sample manager located at a testing location and programmed to:
  i) for each sample of biological material transported in the sample transport container, make history logging information for that sample of biological material available at the testing location, wherein the history logging information is taken from a set of history logs, each of which:
    1) is associated with a single sample of biological material with a unique identifier for that sample of biological material; and
    2) comprises:
      a) a set of measurements of one or more characteristics of the environment of the sample transport container while the associated sample of biological material was in transit; and
      b) a transit initiation timestamp, wherein the transit initiation timestamp is when the associated sample of biological material was placed into the sample transport container for transit;
    and
  ii) provide, based on a level of conformity or non-conformity of a sample of biological material with a set of requirements for a medical diagnostic test, at least one user instruction;
wherein:
A) the set of one or more environment sensors adapted to take measurements of one or more characteristics of the environment of the sample transport container comprises one or more temperature sensors adapted to take temperature measurements of the environment of the sample transport container;
B) the machine comprises a central monitor programmed to maintain the set of history logs by performing acts comprising:
  I) receiving transit data from history loggers for samples of biological material;
  II) storing the transit data for samples of biological material in database records associated with the unique identifiers of each of the samples of biological material to which the transit data relates; and
C) the central monitor is programmed to determine the level of conformity or non-conformity of the sample of biological material with the set of requirements for the medical diagnostic test by performing a set of acts comprising:
  I) using the unique identifier of the sample of biological material, retrieving data indicating that the medical diagnostic test is to be performed with that sample of biological material;
  II) performing a set of comparisons comprising:
    a) comparing temperature data from the set of one or more temperature sensors with a temperature threshold associated with the medical diagnostic test;
    b) comparing how long the sample of biological material had been in transit with a transit time threshold associated with the medical diagnostic test; and
    c) comparing a time delay between when the sample of biological material was collected and when it was placed in transit with a collection delay threshold for the medical diagnostic test;
    and
  III) based on the set of comparisons, determining the level of conformity or non-conformity from a plurality of potential levels of non-conformity, wherein the plurality of potential levels of non-conformity comprises at least two levels in which the sample of biological material does not conform to the set of requirements for the medical diagnostic test.

2. The machine of claim 1, wherein:
a) the set of one or more environment sensors adapted to take measurements of one or more characteristics of the environment of the sample transport container comprise one or more temperature sensors adapted to take temperature measurements of the environment of the sample transport container;
b) the history logging information the sample manager located at the testing location is programmed to make available at the testing location for a sample of biological material comprises:
  i) how many individuals have handled the sample of biological material while in transit;
  ii) duration of time the sample of biological material is in transit; and
  iii) temperature the sample of biological material has been exposed to while in transit.

3. The machine of claim 1, wherein the at least one user instruction is selected from a group consisting of:
a) an instruction to evaluate a result of the medical diagnostic test using a modified evaluation parameter, wherein the modified evaluation parameter is a parameter to evaluate a result of the medical diagnostic test instead of a default evaluation parameter, wherein the modified evaluation parameter is a first level of test product for indicating a positive result which is lower than a default level of test product for indicating a positive result; and
b) an instruction to rerun the medical diagnostic test with the sample of biological material one or more times.

4. The machine of claim 1, wherein:
a) the machine comprises a central monitor programmed to maintain the set of history logs by performing acts comprising incorporating data received from the history loggers into database records associated with unique identifiers of samples of biological material to which that data relates;
b) the set of one or more history loggers comprises:
  i) a first sample manager located at a collection point for samples of biological material; and
  ii) a second sample manager located at a preparation site for samples of biological material;
c) the first sample manager is programmed to send to the central monitor, for each sample of biological material collected at the collection point where the first sample manager is located:

i) a timestamp reflecting when that sample of biological material was collected;
ii) a unique identifier for that sample of biological material;
d) the second sample manager is programmed to, for each sample of biological material received at the preparation site where the second sample manager is located:
i) retrieve, from the central monitor using the unique identifier for that sample of biological material, a set of preparation activities to perform for that sample of biological material; and
ii) present instructions to perform the set of preparation activities for that sample of biological material.

5. The machine of claim 4, wherein:
a) each history logger from the set of one or more history loggers is programmed to:
i) require a user of that history logger to authenticate his or her identity before that history logger could:
1) receive information about samples of biological material taken from patients; and
2) communicate information about samples of biological material taken from patients with either the central monitor or other history loggers;
ii) inform the central monitor of the authenticated identity of the user of that history logger and the unique identifiers of samples of biological material handled by the user of that history logger; and
b) the central monitor is programmed to, based on receiving a message that a sample of biological material has arrived at the testing location, using the unique identifier for the sample of biological material, retrieve data indicating the authenticated identities of all users of history loggers who had handled the sample of biological material.

6. The machine of claim 1, wherein the unique identifiers for the samples of biological material in the history logs comprise, for each sample of biological material transported in the sample transport container, at least one of:
a) an identifier of a sample holder in which that sample of biological material is contained; and
b) an identifier of the sample transport container, combined with an identification of a location in the sample transport container where the sample of biological material is placed.

7. The machine of claim 1, wherein:
a) the sample manager located at the testing location is one of a plurality of sample managers located at a plurality of testing locations;
b) the set of one or more history loggers comprises a plurality of mobile history loggers;
c) the machine comprises a central monitor, wherein the central monitor is communicatively connected to each of the testing locations and is configured to:
i) determine a testing location to which a sample of biological material should be transported based on one or more of:
1) testing time at each of the plurality of testing locations;
2) distance between the sample of biological material and each of the plurality of testing locations; and
3) transit time to each of the plurality of testing locations; and
ii) send a message indicating the testing location to which the sample of biological material should be transported to a mobile history logger of a courier for the sample of biological material.

8. The machine of claim 1, wherein:
a) the set of one or more history loggers comprises a plurality of mobile history loggers, each of which comprises at least one of:
i) a wireless transceiver; or
ii) a wireless receiver and a wireless transmitter;
b) the sample manager at the testing location is programmed to receive the set of history logs from a mobile history logger carried by a courier who delivers the sample transport container to the testing location;
c) the set of one or more history loggers is adapted to maintain the set of history logs using instructions that, when executed by a history logger, cause the history logger which executes the instructions to perform acts comprising:
i) when a user of that history logger takes possession of a sample of biological material from a previous custodian of the sample of biological material, receiving, via a first NFC connection, the history log for the sample of biological material from a history logger used by the previous custodian of the sample of biological material;
ii) updating the history log for the sample of biological material with a timestamp indicating when the user of that history logger takes possession of the sample of biological material; and
iii) when the user of that history logger transfers possession of the sample of biological material to a new custodian, transferring, via a second NFC connection, the history log for the sample of biological material to a history logger used by the new custodian.

9. A method comprising storing a set of programs on one or more non-transitory computer readable mediums, and making a plurality of programs taken from the set of one or more programs available for reproduction and use, wherein the plurality of programs made available for reproduction and use comprises:
a) a first program operable to, when executed, cause a history logger to perform a set of history logging acts comprising receiving transit data, the transit data comprising values of one or more environment characteristics for a sample transport container while samples of biological materials are in transit in the sample transport container;
b) a second program, wherein the second program is operable to, when executed, cause a sample manager to perform a set of sample management acts comprising:
i) receiving a unique identifier corresponding to a sample of biological material;
ii) making history logging information for the sample of biological material corresponding to the received unique identifier available at a location where the sample of biological material is to be tested and/or prepared for testing, wherein the history logging information indicates:
1) a value of at least one of the one or more environment characteristics the first program is operable to cause the history logger to receive when executed; and
2) a period since initiation of transit for the sample of biological material corresponding to the received unique identifier;
and
iii) providing, based on a level of conformity or nonconformity of the sample of biological material with a set of requirements for a medical diagnostic test, at least one user instruction;

wherein:
A) the at least one user instruction is selected from a group consisting of:
  I) an instruction to evaluate a result of the medical diagnostic test using a modified evaluation parameter, wherein the modified evaluation parameter is a parameter to evaluate a result of the medical diagnostic test instead of a default evaluation parameter; and
  II) an instruction to rerun the medical diagnostic test with the sample of biological material one or more times; and
B) the modified evaluation parameter is a first level of test product for indicating a positive result which is lower than a default level of test product for indicating a positive result.

10. The method of claim 9, wherein the set of programs comprises a third program, wherein the third program is operable to, when executed, cause a central monitor to perform a set of central monitor acts comprising:
a) maintaining a set of history logs associated with samples of biological material by performing acts comprising:
  i) receiving transit data for the samples of biological material from the history logger; and
  ii) using the received transit data to update a database comprising records associated with unique identifiers corresponding to the samples of biological material to which the received transit data relates; and
b) responding to requests received from the sample manager and/or other sample managers for information on samples of biological material corresponding to unique identifiers associated with the database records in which the received transit data was stored.

11. The method of claim 10, wherein:
a) the history logger is a smartphone configured with the first program;
b) the sample manager is a computer configured with the second program;
c) the central monitor is a server configured with the third program; and
d) the central monitor is configured to determine a distance between the history logger and the sample manager using a GPS receiver incorporated into the history logger.

12. The method of claim 10, wherein the method comprises at least one act from a set of acts consisting of:
a) making the third program available for reproduction and use; and
b) executing the third program.

13. The method of claim 10, wherein at least one of the programs from the set of programs is operable to, when executed, cause a computer to perform acts comprising determining whether the sample of biological material conforms to the set of requirements for the medical diagnostic test by:
  i) using the unique identifier for the sample of biological material, retrieving data indicating that the medical diagnostic test is to be performed with that sample of biological material;
  ii) comparing temperature data from the database which execution of the third program would cause the central monitor to update with a temperature threshold associated with the medical diagnostic test;
  iii) comparing how long the sample of biological material had been in transit with a transit time threshold associated with the medical diagnostic test; and
  iv) comparing a time delay between when the sample of biological material was collected and when it was placed in transit with a collection delay threshold for the medical diagnostic test.

14. The method of claim 9, wherein:
a) the history loggers are mobile history loggers comprising at least one of:
  i) a wireless transceiver; or
  ii) a wireless receiver and a wireless transmitter
b) the first program is operable, to facilitate transfer of a transported sample of biological material from a first custodian using a first history logger configured by the first program to a second custodian using a second history logger configured by the first program, to:
  i) cause the first history logger to send, via a NFC connection, a history log for the transported sample of biological material to the second history logger; and
  ii) cause the second history logger to update the history log for the transported sample of biological material with a timestamp indicating when the second custodian takes possession of the sample of biological material.

15. A method for enabling logging of information about samples of biological material including measurements captured by one or more environment sensors of characteristics of an environment of a sample transport container used to transport the samples of biological material after they are collected from patients, the method comprising making a plurality of programs available for reproduction and use, wherein the plurality of programs comprises:
a) a first program operable to, when executed, cause a history logger to perform a set of history logging acts comprising receiving transit data, the transit data comprising values of one or more environment characteristics for the sample transport container while the samples of biological material are in transit in the sample transport container;
b) a second program, wherein the second program is operable to, when executed, cause a sample manager to perform a set of sample management acts comprising:
  i) receiving a unique identifier corresponding to a sample of biological material;
  ii) making history logging information for the sample of biological material corresponding to the received unique identifier available at a location where the sample of biological material is to be tested and/or prepared for testing, wherein the set of history logging information indicates:
    1) a value of at least one of the one or more environment characteristics the first program is operable to cause the history logger to receive when executed; and
    2) a period since initiation of transit for the sample of biological material corresponding to the received unique identifier; and
  iii) providing, based on a level of conformity or non-conformity for the sample of biological material with a set of requirements for a medical diagnostic test, at least one user instruction;

wherein:
A) the one or more environment sensors comprise one or more temperature sensors adapted to take temperature measurements of the environment of the sample transport container;
B) the method comprises maintaining, via a central monitor, a set of history logs by performing acts comprising:
  I) receiving transit data from the history logger and/or other history loggers for samples of biological material;
  II) storing the transit data for samples of biological material in database records associated with the unique identifiers of the samples of biological material to which the transit data relates; and
C) the method comprises the central monitor determining the level of conformity or non-conformity of the sample of biological material with the set of requirements for the medical diagnostic test by performing a set of acts comprising:
  I) using the unique identifier of the sample of biological material, retrieving data indicating that the medical diagnostic test is to be performed with that sample of biological material;
  II) performing a set of comparisons comprising:
    a) comparing temperature data from the set of one or more temperature sensors with a temperature threshold associated with the medical diagnostic test;
    b) comparing how long the sample of biological material had been in transit with a transit time threshold associated with the medical diagnostic test; and
    c) comparing a time delay between when the sample of biological material was collected and when it was placed in transit with a collection delay threshold for the medical diagnostic test; and
  III) based on the set of comparisons, determining the level of conformity or non-conformity from a plurality of potential levels of non-conformity, wherein the plurality of potential levels of non-conformity comprises at least two levels in which the sample of biological material does not conform to the set of requirements for the medical diagnostic test.

16. The method of claim 15, wherein the plurality of programs comprises a third program, wherein the third program is operable to, when executed, cause the central monitor and/or other central monitors to perform a set of central monitor acts comprising:
  a) maintaining a set of history logs associated with the samples of biological material by performing acts comprising:
    i) receiving transit data for the samples of biological material from the history logger; and
    ii) using the received transit data to update a database comprising records associated with unique identifiers corresponding to the samples of biological material; and
  b) responding to requests received from the sample manager and/or other sample managers for information on the samples of biological material.

17. The method of claim 16, wherein the at least one of the programs from the plurality of programs made available for reproduction and use which is operable to, when executed, cause the computer to perform the set of alerting acts is selected from a group of programs consisting of:
  a) the second program; and
  b) the third program.

18. The method of claim 15, wherein:
  a) the history logger is a mobile history logger which:
    i) is configured to authenticate an identity of its user with biometric information from that user; and
    ii) comprises at least one of:
      1) a wireless transceiver; or
      2) a wireless receiver and a wireless transmitter; and
  b) the first program is operable, to facilitate transfer of a transported sample of biological material from a first custodian using the history logger to a second custodian using a second history logger configured by the first program, to:
    i) cause the history logger to send, via a NFC connection, a history log for the transported sample of biological material to the second history logger; and
    ii) cause the second history logger to update the history log for the transported sample of biological material with a timestamp indicating when the second custodian takes possession of the sample of biological material.

* * * * *